(12) United States Patent
Richens et al.

(10) Patent No.: US 11,379,747 B1
(45) Date of Patent: Jul. 5, 2022

(54) COUNTERFACTUAL MEASURE FOR MEDICAL DIAGNOSIS

(71) Applicant: Babylon Partners Limited, London (GB)

(72) Inventors: Jonathan George Richens, London (GB); Ciarán Mark Lee, London (GB); Saurabh Johri, London (GB)

(73) Assignee: BABYLON PARTNERS LIMITED, London (GB)

( * ) Notice: Subject to any disclaimer, the term of this patent is extended or adjusted under 35 U.S.C. 154(b) by 159 days.

(21) Appl. No.: 16/938,829

(22) Filed: Jul. 24, 2020

Related U.S. Application Data

(63) Continuation-in-part of application No. 16/520,280, filed on Jul. 23, 2019, now Pat. No. 11,017,905.

(60) Provisional application No. 62/812,226, filed on Feb. 28, 2019.

(51) Int. Cl.
| | | |
|---|---|---|
| *G06N 7/00* | (2006.01) | |
| *G16H 50/50* | (2018.01) | |
| *G06N 5/04* | (2006.01) | |
| *G06N 20/00* | (2019.01) | |

(52) U.S. Cl.
CPC .............. *G06N 7/005* (2013.01); *G06N 5/046* (2013.01); *G06N 20/00* (2019.01); *G16H 50/50* (2018.01)

(58) Field of Classification Search
CPC ........ G16H 50/50; G06N 7/005; G06N 20/00; G06N 5/046
See application file for complete search history.

(56) References Cited

U.S. PATENT DOCUMENTS

| | | |
|---|---|---|
| 2007/0288418 A1 | 12/2007 | Pope |
| 2008/0215367 A1 | 9/2008 | Marshall |
| 2011/0137847 A1 | 6/2011 | Fahner |
| 2014/0046696 A1 | 2/2014 | Higgins et al. |

(Continued)

FOREIGN PATENT DOCUMENTS

| | | |
|---|---|---|
| WO | 2016-094330 A2 | 6/2016 |
| WO | 2016-097886 A1 | 6/2016 |

OTHER PUBLICATIONS

Shpitser, Ilya, "Complete Identification Methods for Causal Hierarchy," Journal of Machine Learning Research 9 (2008) 1941-1979 (Year: 2008).*

(Continued)

*Primary Examiner* — John P Go
(74) *Attorney, Agent, or Firm* — McDermott Will & Emery LLP

(57) ABSTRACT

A method for providing a computer-implemented medical diagnosis includes receiving an input from a user comprising at least one symptom of the user. The method also includes providing the at least one symptom as an input to a medical model, the medical model being retrieved from memory. The medical model includes a probabilistic graphical model comprising probability distributions and relationships between symptoms and diseases. The method also includes performing inference on the probabilistic graphical model to obtain a prediction of the probability that the user has that disease. The method also includes outputting an indication that the user has a disease from the Bayesian inference, wherein the inference is performed using a counterfactual measure.

20 Claims, 18 Drawing Sheets

(56) References Cited

U.S. PATENT DOCUMENTS

| | | | |
|---|---|---|---|
| 2017/0061324 A1* | 3/2017 | Glass | G06N 7/005 |
| 2019/0155993 A1 | 5/2019 | Wilkerson et al. | |
| 2019/0332957 A1* | 10/2019 | Malur Srinivasan | G06N 7/005 |

OTHER PUBLICATIONS

Shpitser, Ilya, "Complete Identification Methods for the Causal Hierarchy," Journal of Machine Learning Research 9 (2008), 1941-1979 (Year: 2008).

Liu, Y., et al., "Passive diagnosis for wireless sensor networks," IEEE/ACM Trans-actions on Networking (TON), vol. 18. No 4, pp. 1132-1144, 2010.

Perreault, L., et al., "A noisy-or model for continuous time bayesian networks.," in FLAIRS Conference, pp. 668-673, 2016.

Arora, S., et al., "Provable learning of noisy-or networks," in Proceedings of the 49th Annual ACM SIGACT Symposium on Theory of Computing, pp. 1057-1066, ACM, 2017.

Abdollahi, A., et al., "Unification of leaky noisy or and logistic regression models and maximum a posteriori inference or multiple fault diagnosis using the unified model," in DX Conference (Denver, Co), 2016.

Pearl, J., "Probabilities of causation: three counterfactual interpretations and their identification," Synthese, vol. 121, vol. 1-2, pp. 93-149, 1999.

Rota, G.C., "On the foundations of combinatorial theory i. theory of mobius functions," Probability theory and related fields, vol. 2, No. 4, pp. 340-368, 1964.

Richens, J. G. et al., "Counterfactual diagnosis," Cornell University, arXiv:1910.06772v3 [Submitted on Oct. 15, 2019 (v1), last revised Mar. 13, 2020 (this version, v3) and can be found at https://arxiv.org/abs/1910.06772, with previous versions of the article].

Johansson, F., et al., "Learning representations for counterfactual inference," in International Conference on Machine Learning, pp. 3020-3029, 2016.

Louizos, C., et al., "Causal effect inference with deep latent-variable models," in Advances in Neural Information Processing Systems, pp. 6446-6456, 2017.

Subbaswamy, A., et al., "Counterfactual normalization: Proactively addressing dataset shift using causal mechanisms," Proceedings of the 34th Conference on Uncertainty in Artificial Intelligence, arXiv:1808.03253, 2018.

Schulam, P., et al., "Reliable decision support using counterfactual models," in Advances in Neural Information Processing Systems, pp. 1697-1708, 2017.

Buesing, L., et al., "Woulda, coulda, shoulda: Counterfactually-guided policy search," arXiv:1811.06272, 2018.

Liang, H., et al., "Evaluation and accurate diagnoses of pediatric diseases using artificial intelligence," Nature medicine, p. 1, 2019.

Topol, E.J., "High-performance medicine: the convergence of human and artificial intelligence," Nature medicine, vol. 25, No. 1, p. 44, 2019.

De Fauw, J., et al., "Clinically applicable deep learning for diagnosis and referral in retinal disease," Nature medicine, vol. 24, No. 9, p. 1342, 2018.

Silver, D., et al., "Mastering the game of go without human knowledge," Nature, vol. 550, No. 7676, p. 354, 2017.

Pearl, J., Causality. Chapter 7, Cambridge university press, 2009.

Trimble, M., et al., "The thinking doctor: clinical decision making in contemporary medicine," Clinical Medicine, vol. 16, No. 4, pp. 343-346, 2016.

Miller, R., "A history of the internist-1 and quick medical reference (qmr) computer-assisted diagnosis projects, with lessons learned," Yearbook of medical informatics, vol. 19, No. 01, pp. 121-136, 2010.

Cai, B., et al., "Bayesian networks in fault diagnosis," IEEE Transactions on Industrial Informatics, vol. 13, No. 5, pp. 2227-2240, 2017.

Yongli, Z., et al., "Bayesian networks-based approach for power systems fault diagnosis," IEEE Transactions on Power Delivery, vol. 21, No. 2, pp. 634-639, 2006.

Dey, S.., et al., "A bayesian network approach to root cause diagnosis of process variations," International Journal of Machine Tools and Manufacture, vol. 45, No. 1, pp. 75-91, 2005.

Cai, B., et al., "Multi-source information fusion based fault diagnosis of ground-source heat pump using bayesian network," Applied energy, vol. 114, pp. 1-9, 2014.

Lauritzen, S. L., Graphical models, vol. 17. pp. 28-32, Clarendon Press, 1996.

Miller, R. A., et al., "The internist-1/quick medical reference project—status report," Western Journal of Medicine, vol. 145, No. 6, p. 816, 1986.

Shwe, M. A., et al., "Probabilistic diagnosis using a reformulation of the internist-1/qmr knowledge base," Methods of Information in Medicine, vol. 30, No. 04, pp. 241-255, 1991.

Heckerman, D. E., et al., "Toward normative expert systems: Part i the pathfinder project," Methods of information in medicine, vol. 31, No. 02, pp. 90-105, 1992.

Morris, Q., "Recognition networks for approximate inference in bn20 networks," in Proceedings of the Seventeenth conference on Uncertainty in artificial intelligence, pp. 370-377, Morgan Kaufmann Publishers Inc., 2001.

Babylon Health, "Babylon health raises further 60m to continue building out ai doctor app," https://techcrunch.com/2017/04/25/babylon-health-raises-further-60m-to-continue-building-out-ai-doctor-app/, 2017.

Semigran, H. L., et al., "Evaluation of symptom checkers for self diagnosis and triage: audit study," bmj, vol. 351, p. h3480, 2015.

Amato, F., et al., "Artificial neural networks in medical diagnosis," 2013.

Das, R., et al., "Effective diagnosis of heart disease through neural networks ensembles," Expert systems with applications, vol. 36, No. 4, pp. 7675-7680, 2009.

Jiang, F., et al., "Artificial intelligence in healthcare: past, present and future," Stroke and vascular neurology, vol. 2, No. 4, pp. 230-243, 2017.

Neyman, J., "On the application of probability theory to agricultural experiments," 1990.

Rubin, D.B., "Bayesian inference for causal effects: The role of randomization," The Annals of statistics, pp. 34-58, 1978.

Richardson, T.S., et al., "Single world intervention graphs (swigs): A unification of the counterfactual and graphical approaches to causality," 2013.

Balke, A., et al., "Counterfactual probabilities: Computational methods, bounds and appli¬cations," in Proceedings of the Tenth international conference on Uncertainty in artificial intelli¬gence, pp. 46-54, Morgan Kaufmann Publishers Inc., 1994.

Shpitser, I., et al., and J. Pearl, "What counterfactuals can be tested," in Proceedings of the Twenty-Third Conference on Uncertainty in Artificial Intelligence, pp. 352-359, AUAI Press, 2007.

Bareinboim, E., et al., "Bandits with unobserved confounders: A causal approach," in Advances in Neural Information Processing Systems, pp. 1342-1350, 2015.

Razzaki, S., et al., "A comparative study of artificial intelligence and human doctors for the purpose of triage and diagnosis," arXiv preprint arXiv:1806.10698, 2018.

Nikovski, D., "Constructing bayesian networks for medical diagnosis from incomplete and partially correct statistics," IEEE Transactions on Knowledge & Data Engineering, No. 4, pp. 509-516, 2000.

Rish, I., et al., "Accuracy vs. efficiency trade-offs in probabilistic diagnosis," in AAAI/IAAI, pp. 560-566, 2002.

Onis'ko, A., et al., "Learning bayesian network parameters from small data sets: Application of noisy-or gates," International Journal of Approximate Reasoning, vol. 27, No. 2, pp. 165-182, 2001.

Halpern, Y., et al., "Unsupervised learning of noisy-or bayesian networks," arXiv preprint arXiv:1309.6834, 2013.

Guyatt, G. H., et al., "Measuring disease-specific quality of life in clinical trials.," CMAJ: Canadian Medical Association Journal, vol. 134, No. 8, p. 889, 1986.

(56) References Cited

OTHER PUBLICATIONS

Pearl, J., "Comment: understanding simpson's paradox," The American Statistician, vol. 68, No. 1, pp. 8-13, 2014.

Wellman, M. P., et al., "Explaining 'explaining away'," IEEE Transactions on Pattern Analysis and Machine Intelligence, vol. 15, No. 3, pp. 287-292, 1993.

Greenland, S., et al., "Causal diagrams for epidemiologic research," Epidemiology, vol. 10, pp. 37-48, 1999.

Shpitser, I., et al., "Effects of treatment on the treated: Identification and generalization," in Proceedings of the twenty-fifth conference on uncertainty in artificial intelligence, pp. 514 521, AUAI Press, 2009.

Morgan, S. L., et al., Counterfactuals and causal inference. Second Edition, Section 2.4, Cambridge University Press, 2015.

Pearl, J., et al., "Causal inference in statistics: An overview," Statistics surveys, vol. 3, pp. 96-146, 2009.

Pearl, J., "The mediation formula: A guide to the assessment of causal pathways in nonlinear models," tech. rep., California Univ Los Angeles Dept of Computer Science, 2011.

Pearl, J., "Direct and indirect effects," in Proceedings of the seventeenth conference on uncertainty in artificial intelligence, pp. 411-420, Morgan Kaufmann Publishers Inc., 2001.

Halpern, J. Y., Actual causality. Section 2.6 MiT Press, 2016.

Shpitser, I., et al., "What counterfactuals can be tested," arXiv preprint arXiv:1206.5294, 2012.

Romessis, C., et al., "Bayesian network approach for gas path fault diagnosis," Journal of engineering for gas turbines and power, vol. 128, No. 1, pp. 64-72, 2006.

Heckerman, D., "A tractable inference algorithm for diagnosing multiple diseases," in Machine Intelligence and Pattern Recognition, vol. 10, pp. 163-171, Elsevier, 1990.

EPO—Notification and of the International Search Report and the Written Opinion for related International Application No. PCT/GB2020/050490 dated May 25, 2020, 12 pgs.

\* cited by examiner

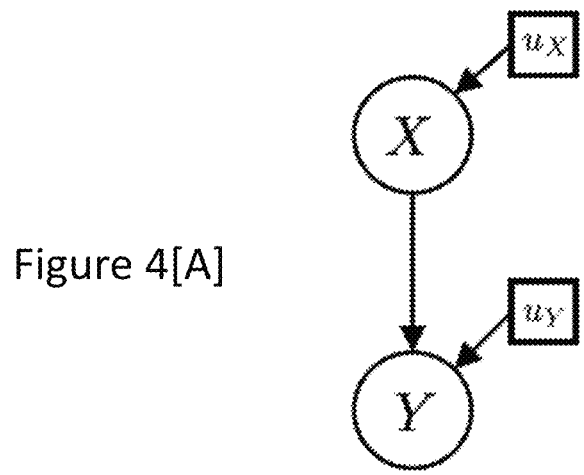
Figure 4[A]
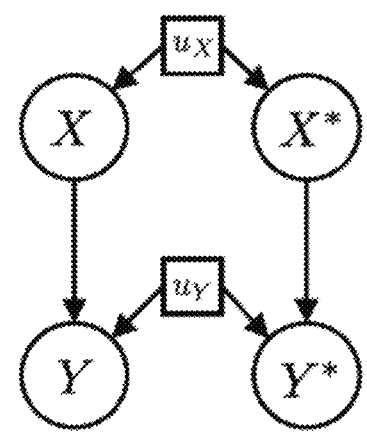
Figure 4[B]
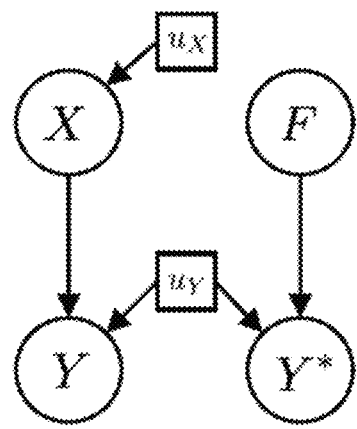
Figure 4[C]

Figure 5[A]
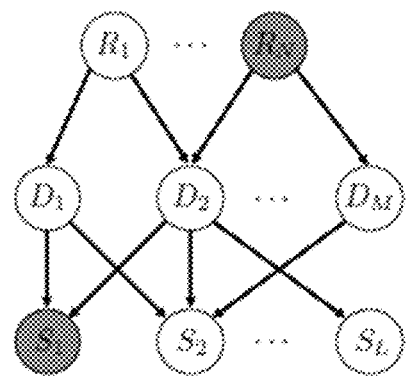
Figure 5[B]
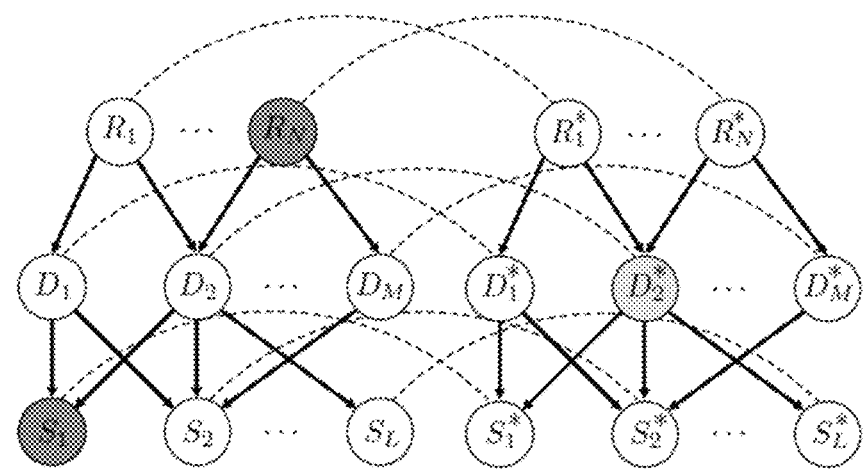
Figure 5[C]
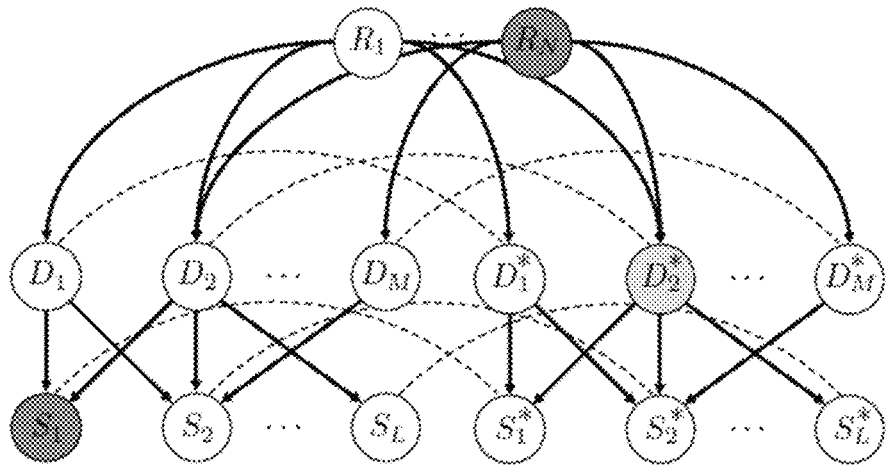

Figure 5[D]
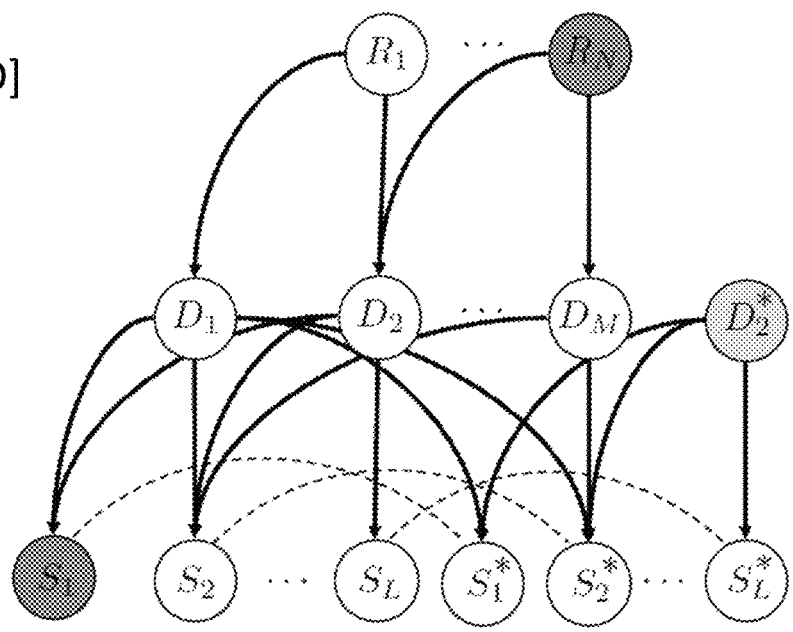
Figure 5[E]
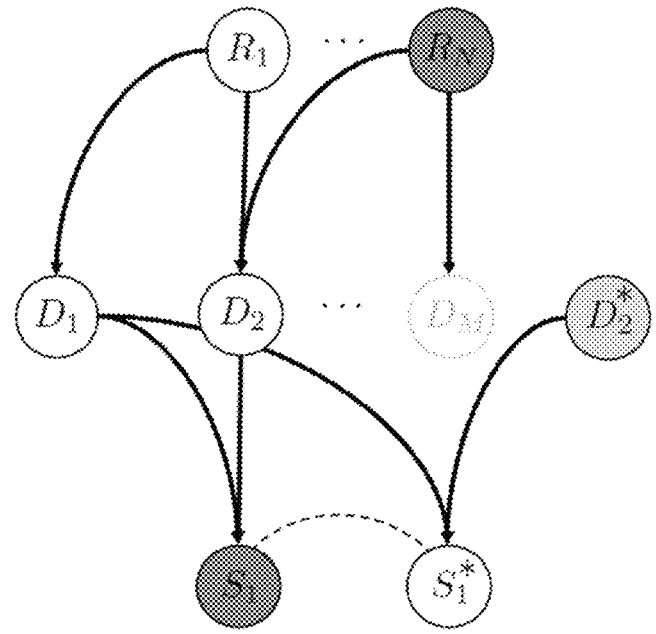

| Agent | Precision |
|---|---|
| Doctor 1 | 0.48 |
| Doctor 2 | 0.59 |
| Doctor 3 | 0.44 |
| Doctor 4 | 0.47 |
| Doctors (Mean) | 0.49 ±0.05 |
| CDM (posterior) | 0.41 |
| CDM (counterfactual) | 0.48 |

Figure 7

|  | Vignettes | | | | | |
|---|---|---|---|---|---|---|
|  | All | VCommon | Common | Uncommon | Rare | VRare |
| N | 1671 | 131 | 413 | 546 | 353 | 210 |
| Mean (A) | 3.81 | 2.85 | 2.71 | 3.72 | 4.35 | 5.45 |
| Mean (C) | 3.16 | 2.5 | 2.32 | 3.01 | 3.72 | 4.38 |
| Wins (A) | 31 | 2 | 7 | 9 | 9 | 4 |
| Wins (C) | 412 | 20 | 80 | 135 | 103 | 69 |
| Draws | 1228 | 131 | 326 | 402 | 241 | 137 |

Figure 12

| Agent | Accuracy (%) | $N_{>D}$ | $N_{>A}$ | $N_{>C1}$ | $N_{>C2}$ |
|---|---|---|---|---|---|
| D | 71.40 ± 3.01 | - | 23 (8) | 12 (4) | 13 (5) |
| A | 72.52 ± 2.97 | 23 (9) | - | 1 (0) | 1 (0) |
| C1 | 77.26 ± 2.79 | 33 (20) | 44 (13) | - | 36 (0) |
| C2 | 77.22 ± 2.79 | 33 (19) | 44 (14) | 32 (0) | - |

Figure 14

Figure 15[A]
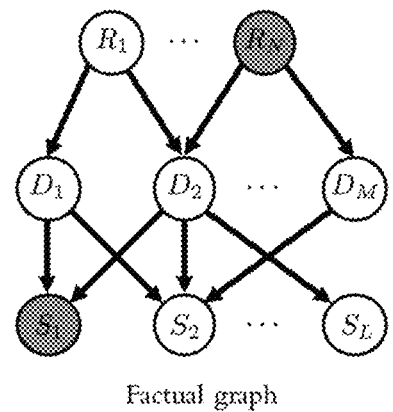
Factual graph
Figure 15[B]
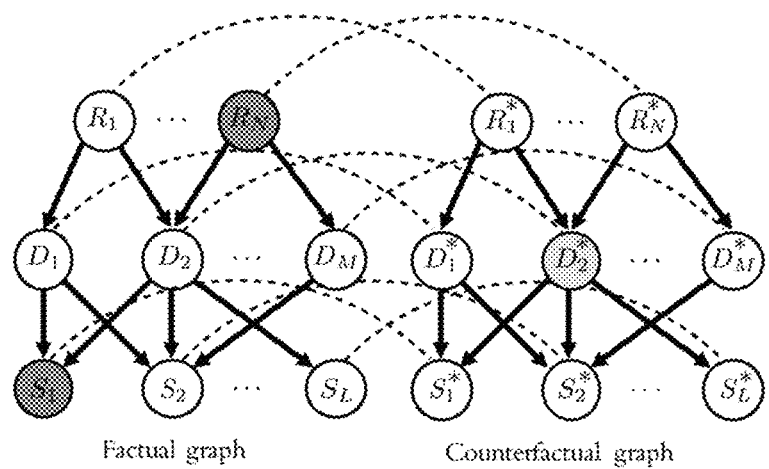
Factual graph          Counterfactual graph
Figure 15[C]
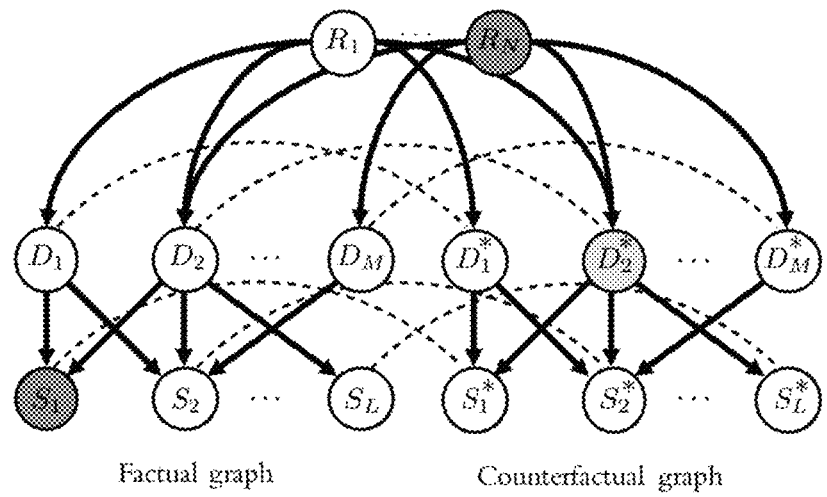
Factual graph          Counterfactual graph Figure 15[D]
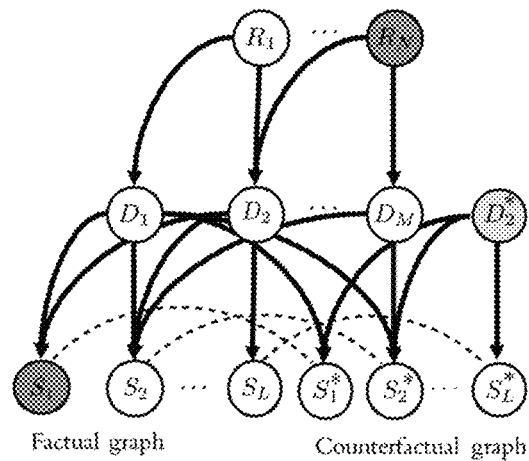
Factual graph    Counterfactual graph
Figure 15[E]
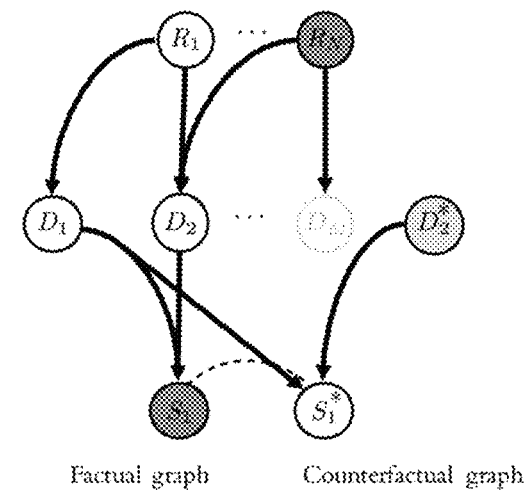
Factual graph    Counterfactual graph
Figure 15[F]
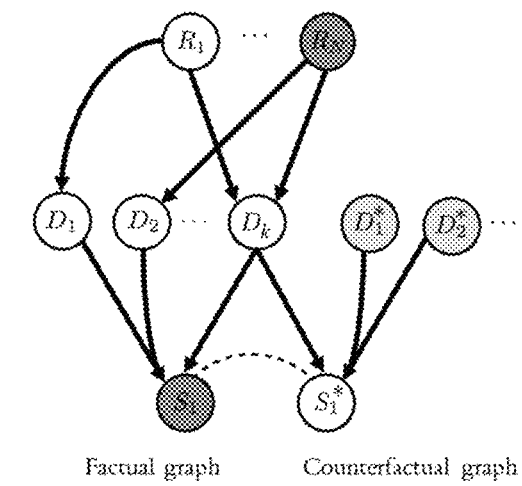
Factual graph    Counterfactual graph Figure 15[G]
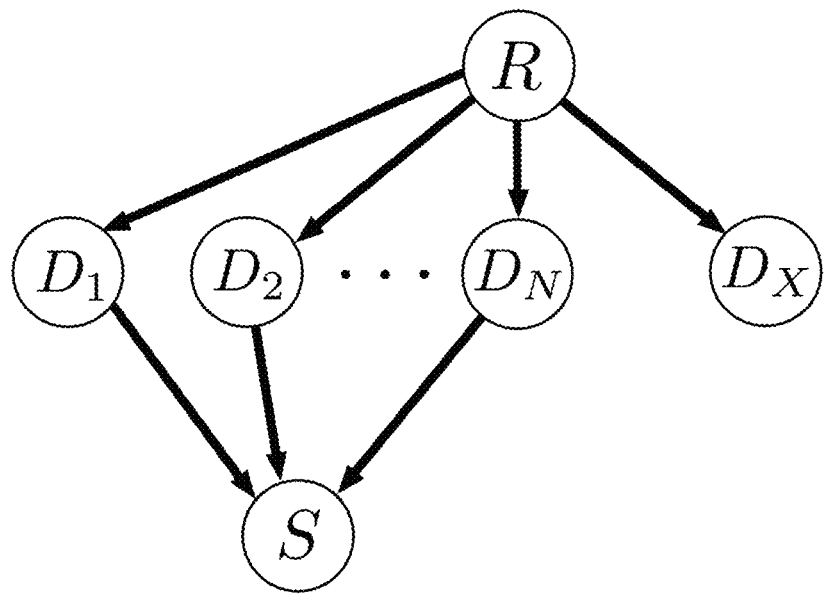
Figure 15[H]
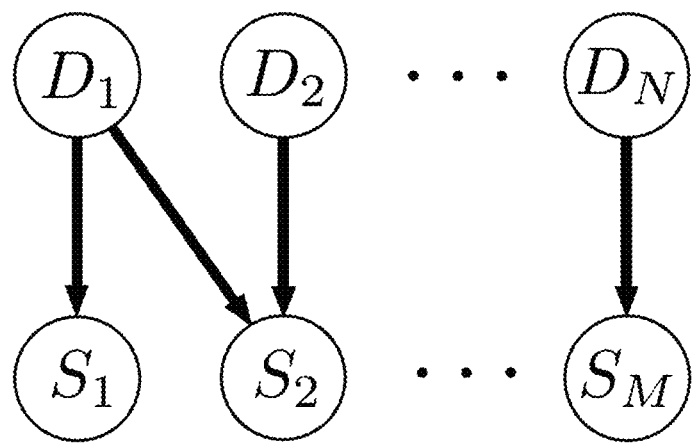

COUNTERFACTUAL MEASURE FOR MEDICAL DIAGNOSIS

CROSS REFERENCE TO RELATED APPLICATIONS

This present application claims the benefit of priority under 35 U.S.C. § 120 as a continuation in part of U.S. patent application Ser. No. 16/520,280, filed Jul. 23, 2019, which claims the benefit of U.S. Provisional Application No. 62/812,226, filed on Feb. 28, 2019, the disclosures of which are hereby incorporated by reference in their entirety for all purposes.

FIELD

Embodiments described herein relate to methods and systems for diagnosis using counterfactual measures.

BACKGROUND

Historically there has been much work towards designing algorithms that can perform medical diagnosis, with models containing hundreds of diseases and symptoms. Recently, there has been renewed hope that these algorithms could eventually surpass the accuracy of human doctors. To achieve this, it is necessary to consider how human doctors perform diagnosis. Given the symptoms presented by the patient and/or relevant knowledge of their background (such as age), a doctor attempts to determine the disease or diseases that are the most likely underlying cause of symptoms presented. This approach is in contrast to the standard method used for algorithmic diagnosis, which involves ranking diseases by their posterior probabilities given the evidence presented, which is referred to as posterior ranking.

BRIEF DESCRIPTION OF THE FIGURES

FIG. 4[A] is a diagram for explaining a twin network;
FIG. 4[B] is a diagram for explaining a twin network;
FIG. 4[C] is a diagram for explaining a twin network;
FIG. 5[A] is a diagram for explaining a twin network;
FIG. 5[B] is a diagram for explaining a twin network;
FIG. 5[C] is a diagram for explaining a twin network;
FIG. 5[D] is a diagram for explaining a twin network;
FIG. 5[E] is a diagram for explaining a twin network;
FIG. 7 is a table showing a comparison of results for counterfactual ranking, posterior ranking and doctor ranking;
FIG. 12 is a table showing the mean position of the true disease for an associative algorithm and a counterfactual algorithm;
FIG. 13[B] is a plot showing a comparison of results for counterfactual ranking against doctor ranking;
FIG. 14 is a table showing group mean accuracy of doctors, associative algorithms, and counterfactual algorithms;
FIG. 15[A] is a diagram for explaining a twin network;
FIG. 15[B] is a diagram for explaining a twin network;
FIG. 15[C] is a diagram for explaining a twin network;
FIG. 15[D] is a diagram for explaining a twin network;
FIG. 15[E] is a diagram for explaining a twin network;
FIG. 15[F] is a diagram for explaining a twin network;
FIG. 15[G] is a diagram of a simple probabilistic graphical model;
and
FIG. 15[H] is a diagram of a two-layer noisy-OR diagnostic network.

DETAILED DESCRIPTION

Figure 1:
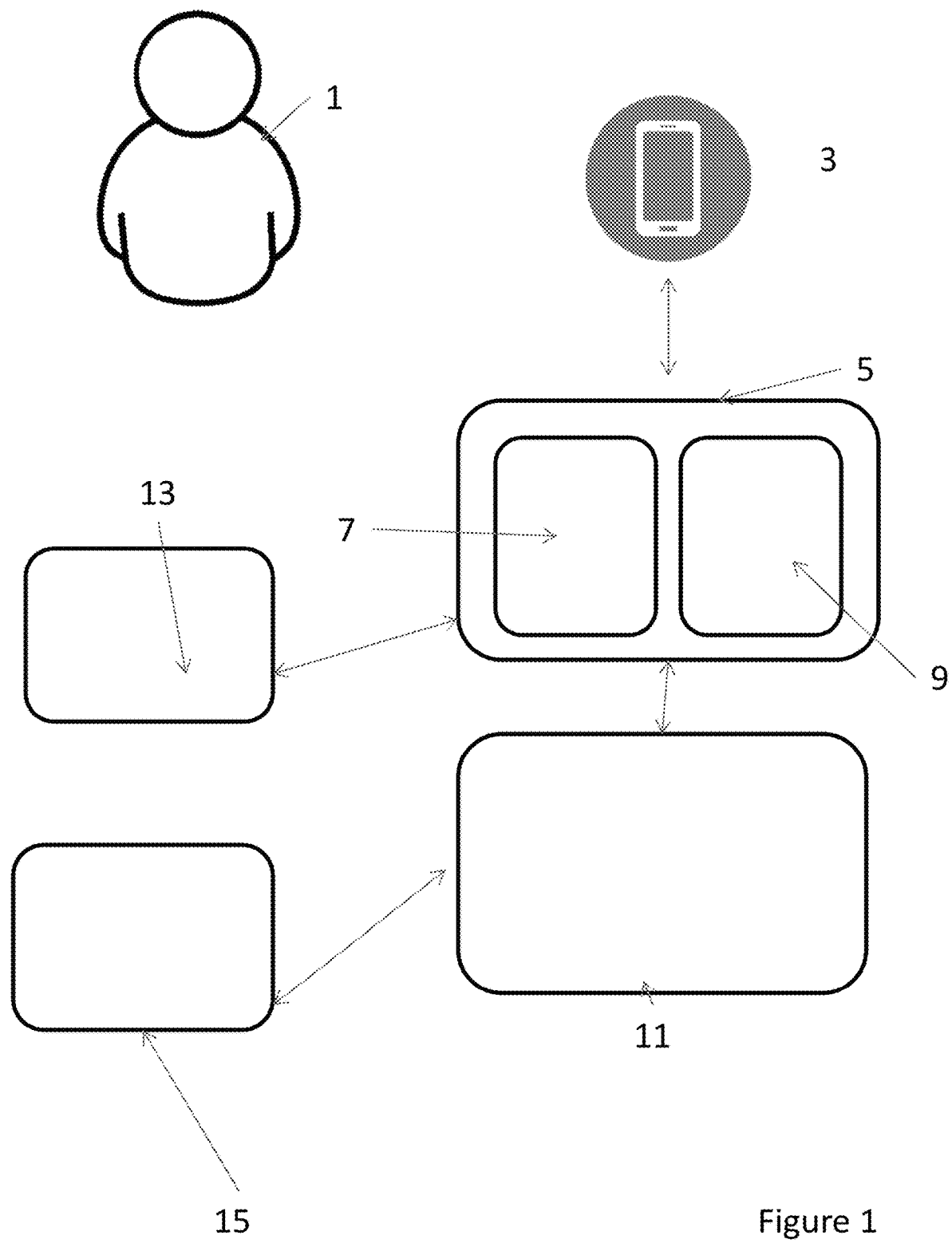
FIG. 1 is a schematic of a system in accordance with an embodiment.

In an embodiment, a method for providing a computer implemented medical diagnosis, the method comprising:
receiving an input from a user comprising at least one symptom of the user;
providing the at least one symptom as an input to a medical model, the medical model being retrieved from memory, the medical model comprising:
a probabilistic graphical model comprising probability distributions and relationships between symptoms and diseases;
performing inference on the probabilistic graphical model to obtain a prediction of the probability that the user has that disease; and
outputting an indication that the user has a disease from the Bayesian inference, wherein the inference is performed using a counterfactual measure.

The disclosed system provides an improvement to computer functionality by allowing computer performance of a function not previously performed by a computer. Specifically, the disclosed system provides for a diagnosis system that can provide counterfactual diagnosis that can provide better accuracy in diagnosis. Also, some of the embodiments allows a computationally more efficient diagnosis.

Although, medical diagnosis is exemplified in the description, the method can be applied to any diagnostic problem.

In one embodiment, the counterfactual measure is the expected disablement. In a further embodiment, the probabilistic graphical model is a NoisyOr model.

In a further embodiment, the counterfactual measure is the expected disablement and the probabilistic graphical model is a NoisyOr model. This combination allows a closed form solution that only requires knowledge of the observational statistics, as is the case for posterior ranking.

In a yet further embodiment, approximate inference techniques are used, for example, importance sampling. In a yet further embodiment, performing inference comprises using a discriminative model pre-trained to approximate the probabilistic graphical model, the discriminative model being trained using samples from said probabilistic graphical model;
deriving estimates, from the discriminative model, that the user has a disease;

performing approximate inference on the probabilistic graphical model to obtain an indication that the user has that disease using the estimate from the discriminative model.

In a further embodiment, the results of predictions of the diseases from the probabilistic graphical model are ranked using the counterfactual measure.

In a further embodiment, the probabilistic graphical model may be a so-called a twin network. The use of a twin network reduces computing counterfactual statements to performing Bayesian inference on an associated causal model.

In a further embodiment, the probabilistic graphical model is a twin network, and the counterfactual measure is the expected disablement. In a further embodiment, the probabilistic graphical model is a twin network, the counterfactual measure is the expected disablement and the probabilistic graphical model is a NoisyOr model.

In a further embodiment, a system for providing a computer implemented medical diagnosis is provided, the system comprising a processor and a memory, the processor being adapted to:
receive an input from a user comprising at least one symptom of the user;
provide the at least one symptom as an input to a medical model, the medical model being retrieved from memory, the medical model comprising: a probabilistic graphical model being stored in memory comprising probability distributions and relationships between symptoms and diseases;
perform inference on the probabilistic graphical model to obtain a prediction of the probability that the user has that disease; and
output an indication that the user has a disease from the Bayesian inference, wherein the inference is performed using a counterfactual measure.

In a further embodiment, a method of forming a twin model that is a graphical representation for computing a counterfactual measure for medical diagnosis is provided. The method comprising: receiving a set of data; creating a first graphical representation from the set of data, the first graphical representation comprising a plurality of first nodes indicating symptoms, risk factors and diseases, the first graphical representation indicating a relationship between the symptoms, the risk factors and the diseases; creating a second graphical representation, wherein the second graphical representation is a copy of the first graphical representation, the second graphical representation comprising a plurality of second nodes indicating the symptoms, the risk factors and the diseases; combining the first graphical representation and the second graphical representation to create said twin model; and setting an intervention node of the plurality of second nodes in the twin model to a value so that inference can be performed on the twin model to obtain a prediction of the probability that a user of the model has a specified disease.

This approach massively amortizes the standard inference cost of calculating counterfactuals by abduction, action and prediction, which would otherwise be intractable for large clinical diagnostic models (CDMs).

In a yet further embodiment, each node in the plurality of first nodes is associated with a latent variable, and the method further comprises: linking the first graphical representation and the second graphical representation by sharing the latent variables of each node of the plurality of first nodes with a corresponding node in the plurality of second nodes.

In a yet further embodiment, the first graphical representation and the second graphical representation are probabilistic graphical models.

In a yet further embodiment, the first graphical representation and the second graphical representation are NoisyOr models.

In a yet further embodiment, the method further comprises: merging a node from the plurality of first nodes with its corresponding node in the plurality of second nodes so as to simplify the twin model.

In a yet further embodiment, the method further comprises: merging a node from the plurality of first nodes with its corresponding node in the plurality of second nodes so as to simplify the twin model.

In a yet further embodiment, after setting the intervention node of the plurality of second nodes in the twin model to a value, the method further comprises: when a node from the plurality of second nodes has identical latent variables and identical parent nodes as its corresponding node in the plurality of first nodes, merging the node with its corresponding node so as to simplify the twin model.

In an additional embodiment, a method for providing a computer implemented medical diagnosis is provided, the method comprising: receiving an input from a user comprising at least one symptom of the user; providing the at least one symptom as an input to a medical model, the medical model being retrieved from memory, the medical model comprising: a probabilistic graphical model comprising probability distributions and causal relationships between symptoms and diseases; performing counterfactual inference on the probabilistic graphical model to obtain a prediction of the probability that the user has a disease; and outputting a counterfactual measure determined from the counterfactual inference, wherein the counterfactual measure is based on whether one or more symptoms would be expected to be present if a first one or more diseases were cured; wherein the probabilistic graphical model is a twin network, the twin network formed by: creating a first graphical representation from a set of data, the first graphical representation comprising a plurality of first nodes indicating symptoms, risk factors and diseases, the first graphical representation indicating a relationship between the symptoms, the risk factors and the diseases, the first graphical representation indicating real variables; creating a second graphical representation, wherein the second graphical representation is a copy of the first graphical representation, the second graphical representation comprising a plurality of second nodes indicating the symptoms, the risk factors and the diseases, the second graphical representation indicating counterfactual states of the real variables; and combining the first graphical representation and the second graphical representation by the sharing of exogenous causes to create said twin network.

In a further additional embodiment, the counterfactual measure is for a second one or more diseases, and wherein the first one or more diseases are possible causes of the one or more symptoms other than the second one or more diseases.

In a further additional embodiment, the counterfactual measure is for the first one or more diseases.

In a further additional embodiment, the counterfactual measure is based on the number of the one or more symptoms that would be expected to be present if the one or more diseases were cured.

In a further additional embodiment, the counterfactual measure is based on the number of the one or more symptoms that would not be expected to be present if the one or more diseases were cured.

In a further additional embodiment, the counterfactual measure is based on the probability that the one or more symptoms would be present if the one or more diseases were cured.

In a further additional embodiment, the counterfactual measure is based on the probability that the one or more symptoms would not be present if the one or more diseases were cured.

In a further additional embodiment, the counterfactual measure is an expected sufficiency. In a further additional embodiment, the counterfactual measure is an expected disablement. In a further additional embodiment, the probabilistic graphical model is a NoisyOr model.

In a further additional embodiment, performing counterfactual inference comprises: using a discriminative model pre-trained to approximate the probabilistic graphical model, the discriminative model being trained using samples from said probabilistic graphical model; deriving estimates, from the discriminative model, that the user has a disease; performing approximate inference on the probabilistic graphical model to obtain an indication that the user has that disease using the estimate from the discriminative model.

In a further additional embodiment, results of predictions of diseases from the probabilistic graphical model are ranked using the counterfactual measure.

In a further additional embodiment, the probabilistic graphical model is a twin network, and the probabilistic graphical model is a NoisyOr model.

In a further additional embodiment, the counterfactual inference further comprises: (1) an abduction step comprising updating a distribution of exogenous latent variables in the twin network based on the at least one symptom; (2) an action step comprising applying a do-operation to a node indicating the disease in the second representation of the updated twin model updated from (1); and (3) a prediction step comprising using the modified twin network from (2) to compute the probability that the user would have the disease.

In another additional embodiment, a system for providing a computer implemented medical diagnosis is provided, the system comprising a processor and a memory, the processor being adapted to: receive an input from a user comprising at least one symptom of the user; provide the at least one symptom as an input to a medical model, the medical model being retrieved from memory, the medical model comprising: a probabilistic graphical model being stored in memory comprising probability distributions and causal relationships between symptoms and diseases, perform counterfactual inference on the probabilistic graphical model to obtain a prediction of the probability that the user has a disease; and output a counterfactual measure determined from the counterfactual inference, wherein, the counterfactual measure is based on whether one or more symptoms would be expected to be present if a first one or more diseases were cured, wherein the probabilistic graphical model is a twin network, the twin network formed by: creating a first graphical representation from a set of data, the first graphical representation comprising a plurality of first nodes indicating symptoms, risk factors and diseases, the first graphical representation indicating a relationship between the symptoms, the risk factors and the diseases, the first graphical representation indicating real variables; creating a second graphical representation, wherein the second graphical representation is a copy of the first graphical representation, the second graphical representation comprising a plurality of second nodes indicating the symptoms, the risk factors and the diseases, the second graphical representation indicating counterfactual states of the real variables; and combining the first graphical representation and the second graphical representation by the sharing of exogenous causes to create said twin network.

In a yet further additional embodiment, a non-transitory carrier medium is provided, the non-transitory carrier medium carrying computer readable instructions being adapted to cause a computer to perform: receiving an input from a user comprising at least one symptom of the user; providing the at least one symptom as an input to a medical model, the medical model being retrieved from memory, the medical model comprising: a probabilistic graphical model comprising probability distributions and causal relationships between symptoms and diseases; performing counterfactual inference on the probabilistic graphical model to obtain a prediction of the probability that the user has a disease; and outputting a counterfactual measure determined from the counterfactual inference, wherein, the counterfactual measure is based on whether one or more symptoms would be expected to be present if a first one or more diseases were cured, wherein the probabilistic graphical model is a twin network, the twin network formed by: creating a first graphical representation from a set of data, the first graphical representation comprising a plurality of first nodes indicating symptoms, risk factors and diseases, the first graphical representation indicating a relationship between the symptoms, the risk factors and the diseases, the first graphical representation indicating real variables; creating a second graphical representation, wherein the second graphical representation is a copy of the first graphical representation, the second graphical representation comprising a plurality of second nodes indicating the symptoms, the risk factors and the diseases, the second graphical representation indicating counterfactual states of the real variables; and combining the first graphical representation and the second graphical representation by the sharing of exogenous causes to create said twin network.

In a yet further additional embodiment, the counterfactual measure is for a second one or more diseases, and wherein the first one or more diseases are possible causes of the one or more symptoms other than the second one or more diseases.

In a yet further additional embodiment, the counterfactual measure is the number of the one or more symptoms that would be expected to be present if the one or more diseases were cured.

In a yet further additional embodiment, the counterfactual measure is the expected sufficiency.

In a yet further additional embodiment, the probabilistic graphical model is a Noisy-Or model.

FIG. 1 is a schematic of a diagnostic system. In one embodiment, a user 1 communicates with the system via a mobile phone 3. However, any device could be used, which is capable of communicating information over a computer network, for example, a laptop, tablet computer, information point, fixed computer etc.

The mobile phone 3 will communicate with interface 5. Interface 5 has 2 primary functions, the first function 7 is to take the words uttered by the user and turn them into a form that can be understood by the inference engine 11. The second function 9 is to take the output of the inference engine 11 and to send this back to the user's mobile phone 3.

In some embodiments, Natural Language Processing (NLP) is used in the interface 5. NLP helps computers interpret, understand, and then use everyday human language and language patterns. It breaks both speech and text down into shorter components and interprets these more manageable blocks to understand what each individual component means and how it contributes to the overall meaning, linking the occurrence of medical terms to the Knowledge Graph. Through NLP it is possible to transcribe consultations, summarise clinical records and chat with users in a more natural, human way.

However, simply understanding how users express their symptoms and risk factors is not enough to identify and provide reasons about the underlying set of diseases. For this, the inference engine 11 is used. The inference engine is a powerful set of machine learning systems, capable of reasoning on a space of >100s of billions of combinations of symptoms, diseases and risk factors, per second, to suggest possible underlying conditions. The inference engine can provide reasoning efficiently, at scale, to bring healthcare to millions.

In an embodiment, the Knowledge Graph 13 is a large structured medical knowledge base. It captures human knowledge on modern medicine encoded for machines. This is used to allows the above components to speak to each other. The Knowledge Graph keeps track of the meaning behind medical terminology across different medical systems and different languages.

In an embodiment, the patient data is stored using a so-called user graph 15.

Clinical diagnostic models (CDMs) can be probabilistic graphical models (PGMs) that model hundreds of diseases, risk factors (the causes of diseases), and symptoms, as binary nodes.

Figure 2:
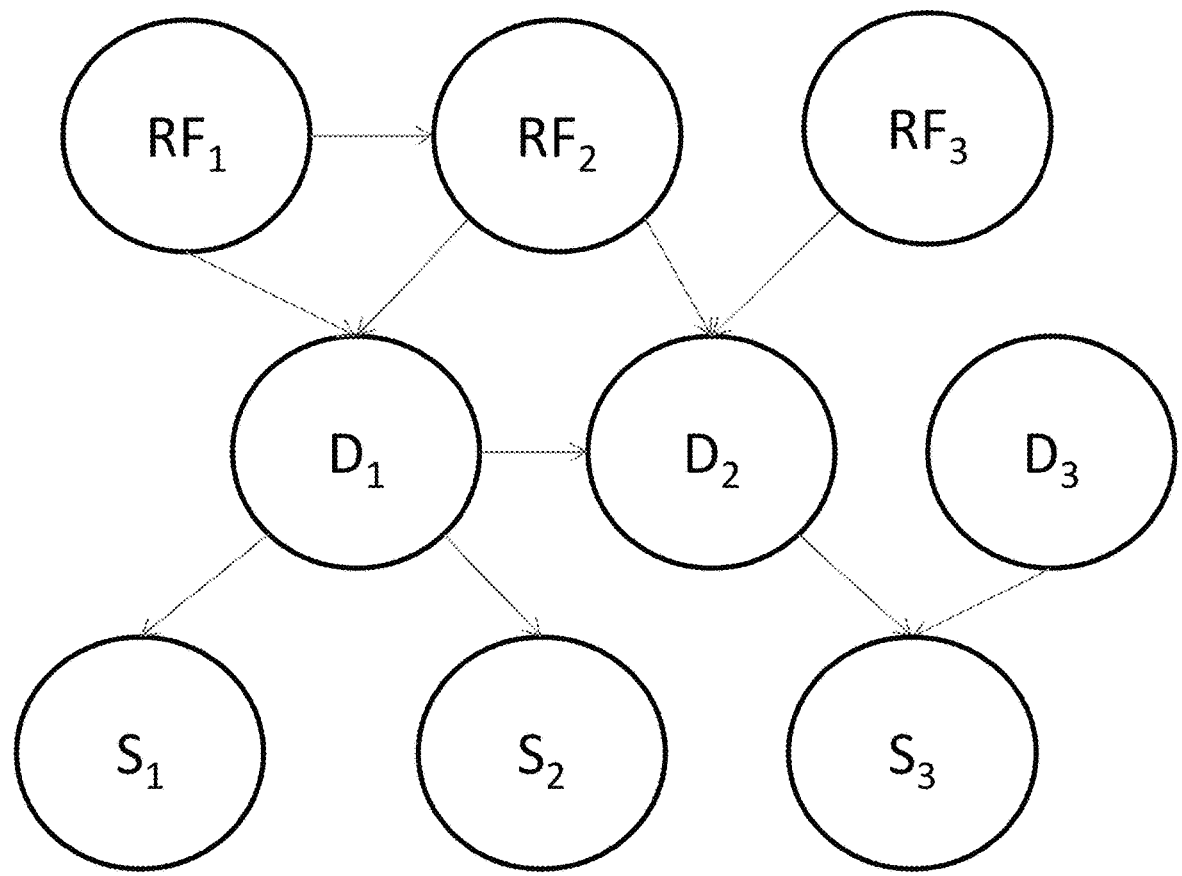
FIG. 2 is a diagram of a probabilistic graphical model of the type that can be used with the system of FIG. 1.

FIG. 2 is a depiction of a graphical model of the type used in the system of FIG. 1. The graphical model provides a natural framework for expressing probabilistic relationships between random variables, to facilitate causal modelling and decision making. In the model of FIG. 2, when applied to diagnosis, D stands for diagnosis, S for symptom and RF for Risk Factor. Three layers: risk factors, diseases and symptoms. Risk factors causes (with some probability) influence other risk factors and diseases, diseases causes (again, with some probability) other diseases and symptoms. There are prior probabilities and conditional marginals that describe the "strength" (probability) of connections. In embodiments, noisy-OR and noisy-MAX modelling assumptions are used.

Most widely used is the noisy-or assumption, as it closely fits the belief about how diseases develop, and allows large PGMs to be efficiently learned and stored. For a variable Y with parents $X_1, \ldots, X_N$, noisy-or assumes that Y=1 if any of its parents activate it A parent X activates its child if i) the parent is 'on', X=1, and ii) the activation succeeds, with an independent probability of failure $X_{X \backslash ,Y}$. Further details of the noisy-or model are provided below.

In this simplified specific example, the model is used in the field of diagnosis. In the first layer, there are three nodes $S_1$, $S_2$ and $S_3$, in the second layer there are three nodes $D_1$, $D_2$ and $D_3$ and in the third layer, there are two nodes $RF_1$, $RF_2$ and $RF_3$.

In the graphical model of FIG. 2, each arrow indicates a dependency. For example, Di depends on $RF_1$ and $RF_2$. $D_2$ depends on $RF_2$, $RF_3$ and $D_1$. Further relationships are possible. In the graphical model shown, each node is only dependent on a node or nodes from a different layer. However, nodes may be dependent on other nodes within the same layer.

In an embodiment, the graphical model of FIG. 2 is a Bayesian Network or probabilistic graphical model "PGM". In this Bayesian Network (or PGM), the network represents a set of random variables and their conditional dependencies via a directed acyclic graph. Thus, in the network of FIG. 2, given full (or partial) evidence over symptoms $S_1$, $S_2$ and $S_3$ and risk factors $RF_1$, $RF_2$ and $RF_3$ the network can be used to represent the probabilities of various diseases $D_1$, $D_2$, and $D_3$.

Causal knowledge is crucial for effective reasoning in many areas of science and medicine. This is due to the fact that causal relations, unlike correlations, allow one analyse the consequences of interventions and treatments. When performing a primary diagnosis, a clinician aims to explain a patients presented symptoms by determining the most likely underlying diseases causing them. Despite this, all previous approaches to Machine Learning assisted diagnosis, including both model-based Bayesian and Deep Learning approaches, fail to incorporate causal knowledge in the diagnosis procedure. The embodiments described herein detail a new diagnostic method based on counterfactual inference, which captures the causal aspect of diagnosis overlooked by previous approaches. Whilst previous approaches fail to match human doctors, the counterfactual method achieves expert clinical accuracy.

The embodiments described herein are largely concerned with the PGM. Specifically, methods are presented which instead of using posterior ranking, a counterfactual measure is instead used and inference is performed on this.

Structural causal models (SCMs) can represent variables as functions of their direct causes, along with an unobserved 'noise' variable that is responsible for their randomness.

To understand the differences, a background on PGMs will be given:

Definition 1. A structural causal model (SCM) specifies:
1. a set of independent latent variables $U=\{u_1; \ldots ; u_n\}$ distributed according to $$P(U) = \prod_i p(u_i),$$

2. a set of observed variables $V=\{v_1; \ldots ; v_n\}$;
3. a directed acyclic graph G, called the causal structure of the model, whose nodes are the variables $U \cup V$
4. a collection of functions $F=\{f_1; \ldots ; f_n\}$ such that every observed variable is a function of its parents together with a latent 'noise' term $$v_i = f_i(Pa(v_i); u_i);$$

where $Pa_i$ denotes the parent nodes of the $i^{th}$ observed variable from G.

The latent noise term appearing in each $f_i$ can be suppressed into $Pa(v_i)$ by enforcing the convention that every observed node has an independent latent variable as a parent in G without loss of generality. This convention is adopted throughout the following.

As every observed variable has an independent latent variable as a parent, the distribution over latents induces a distribution over observed variables through the functions F. That is $$p(v_i) = \sum_{u|v_i = f_i(u)} P(u).$$

As P(U) factorises over each element of U, the joint distribution over every node in G factors into conditional distributions for each variable given its parents $$P(v_i, \ldots, v_n, u_1, \ldots, u_m) = \prod_i p(v_i | \mathrm{Pa}_i) \prod_k p(u_k).$$

Hence, once all exogenous latent variables are marginalized over, an SCM describes a Bayesian network. Any Bayesian network can be constructed in this manner from some underlying SCM. Conversely, SCMs can be viewed as a refinement of Bayesian networks to include the details of the underlying generative functions—a redundant feature in Bayesian networks when calculating observational probabilities but vital for calculating counterfactuals.

In order to formally define a counterfactual query, a "do-operator," an interventional primitive is first defined.

Consider a SCM with functions F. The effect of intervention $do(X=x)$ in this model corresponds to creating a new SCM with functions $F_{x=x}$, formed by deleting from F all functions $f_i$ corresponding to members of the set X and replacing them with the set of constant functions X=x. That is, the do-operator forces variables to take certain values, regardless of the original causal mechanism. Probabilities involving the do-operator, such as $P(Y=y|do(X=x))$ corresponds to evaluating ordinary probabilities in the SCM with functions $F_X$, in this case $P(Y=y)$.

Counterfactual queries tell us the probability that certain outcomes would have occurred had some precondition been different. Given some observations $\varepsilon=e$, the likelihood is calculated that a different outcome $\varepsilon=e'$ (counter to the facts of $\varepsilon=e$) would have been observed given that some hypothetical intervention $do(T=t)$ had taken place. Here $do(T=t)$ is used to denote the intervention to fix variable T=t as defined by Pearl's calculus of interventions [27]. This counterfactual is summarised by the probability $$P(\varepsilon=e'|\varepsilon=e, do(T=t))$$

Counterfactuals allow the quantification of the causal affect of hypothetical interventions on latent variables. For example, it could be asked what is the likelihood that a symptom would not be present, given that the symptom is observed and a disease D, in some unknown state, was treated. This is determined by the counterfactual probability $P(S=F|S=T, do(D=F))$. If D=T is likely to be causing S=T, i.e. the disease is a good causal explanation of the symptom, then this probability will be high. On the other hand, disease hypotheses that are likely given the symptoms but a poor causal explanation will result in low probabilities.

Definition 2 (Counterfactual). Let X and Y be two subsets of variables in V. The counterfactual sentence "Y would be y (in situation U), had X been x," is the solution Y=y of the set of equations $F_x$, succinctly denoted $Y_x(U)=y$.

As with observed variables in Definition 1, the latent distribution P(U) allows one to define the probabilities of counterfactual statements.

$$P(Y_x = y) = \sum_{u|Y_x(u)=y} P(u). \qquad (1)$$

It is possible to implement an algorithmic procedure for computing arbitrary counterfactual queries. First, the distribution over latents is updated to account for the observed evidence. Second, the do-operator is applied. Third, the new causal model created by the application of the do-operator in the previous step is combined with the updated latent distribution to compute the counterfactual query.

The above steps can be summarised as follows (where E denotes the set of real evidence):

(1) (abduction) The distribution of the exogenous latent variables P(u) is updated to obtain P(u|ε)

(2) (action) Apply the do-operation to the variables in set X, replacing the equations $X_i=f_i(Pa(x_i),u_i)$ with $X_i=x_i \forall X_i \in X$.

(3) (prediction). Use the modified model to compute the probability of Y=y.

The first step, updating the distribution over latents and storing the resulting probabilities, requires a large amount of computational resources and memory—especially as conditioning on evidence induces correlations between initially uncorrelated latents. Moreover, as this step has to be repeated for every new counterfactual query, such computational resources are continually required. Therefore, the first step, updating the exogenous latents, is intractable for large models with significant tree-width such as diagnostic networks.

In an embodiment, it is possible to avoid this computationally expensive step by reducing the computing of counterfactual statements to performing Bayesian inference on an associated causal model, known as a twin network.

The twin network method employs two interlinked networks, one representing the real world and the other the counterfactual world being queried. These two networks are identical in structure and share the same latent variables—as the latents are not modified by interventions on the observed variables. The observable variables from the original model are duplicated and labeled distinctly, as they may obtain different values in the real and counterfactual models. After the counterfactual world undergoes the desired intervention, computing a counterfactual statement in the original model is reduced to performing Bayesian inference in the twin network, as the variables in the real and counterfactual worlds can be explicitly compared. The construction of twin networks is discussed further below.

In Pearl, J. 2018. Theoretical impediments to machine learning with seven sparks from the causal revolution. arXiv preprint arXiv:1801.04016), Pearl refers to a "hierarchy" of queries that can be asked about probabilistic models: associative/observational, causal, and counterfactual.

Associative queries lie at the first level of the hierarchy, allowing us only to ask purely observational or "what happened" questions.

This is the domain of Bayesian networks and statistics. Causal queries lie at the second level and concern asking interventional, or "what if", questions, formalised using the do-operator. At the top of the hierarchy are counterfactual, or "why", questions. These allow us to ask causal questions about hypothetical interventions, whilst taking into account real evidence—often in apparent contradiction to our desired interventions.

Consider the question "I have not taken an Asprin, A=false. If I had, would my headache H have gone away?".

This query can be written as $p(H_{A=true}=false|A=false)$ where $H_{A=a}$ is 'the value of H if A had taken value a'.

Note that the evidence state, A=true, differs from the hypothetical intervention state Â=false—a feature that cannot be represented by any purely causal or observational question. Although we posit a different hypothetical state Â=true to the evidence state A=false, the evidence state is still relevant as it provides information about other variables in our model, such as confounding influences between A and H It is this feature that separates counterfactual queries from causal queries Diagnosis—Posterior Ranking Diagnosis can be performed using a CDM by posterior ranking. Given a patients observed risk-factors R and symptoms S, the posteriors of all model diseases are computed, p(Di=T|R,S), and the most likely diseases returned as a differential. Other factors may be used as well as the posterior likelihood in constructing the final differential, such as disease cruelty, but the posteriors are the key ingredient supplied by the CDM.

Bayesian networks represent arguably the best method for performing algorithmic diagnosis—as they are interpretable and can model a very large number of diseases simultaneously.

The next section will explain how they are used to perform diagnosis via the ranking of disease posteriors given evidence, and give examples of where this approach fails to capture the true diagnostic procedure.

Figure 3:
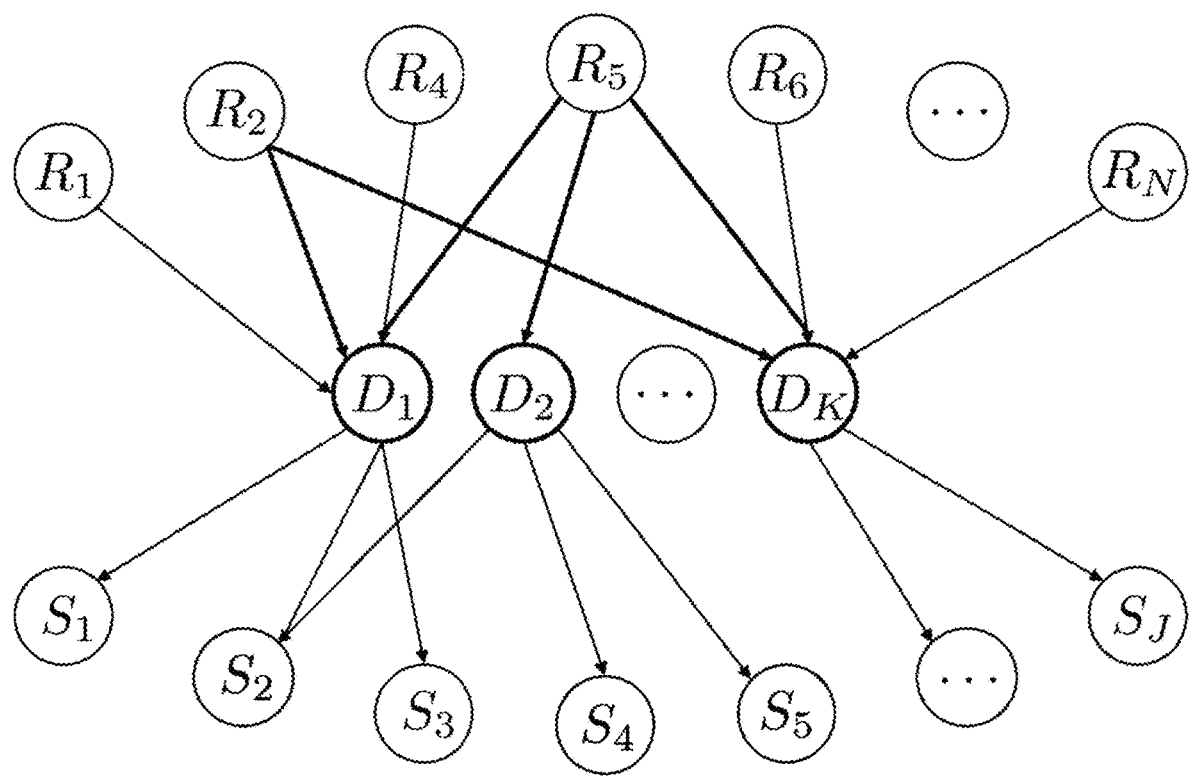
FIG. 3 is a diagram of a PGM for explaining the counterfactual diagnosis method in accordance with an embodiment.

FIG. 3 depicts a typical three-layer Bayesian network used for diagnosis. The top layer is populated by risk factor nodes, such as smoking or a family history of heart disease, representing variables that have a direct causal influence on the diseases. The diseases are found in the middle layer with the bottom layer corresponding to symptoms. For each disease, its children are the symptoms caused by that disease.

The top layer nodes are risk factors, which represent population variables, such as smoking and fitness, that have causal influences on diseases—which constitute the middle layer of nodes. The bottom layer correspond to symptoms, which are caused by underlying diseases. Thick wires highlight back-door paths between diseases $D_1$, $D_2$ and $D_K$ FIG. 3 is just an example of one network. Simpler diagnostic networks can been employed, such as Bayesian networks which have no risk factor layer and stipulate no correlations between diseases. Networks with greater topological complexity can also be considered, such as those exhibiting disease-disease connections—allowing for inter-disease causal effects.

For the Diagnosis is performed on three-layer networks as follows.

A patient supplies evidence which may include known risk factors, symptoms and possibly some known diseases. These evidence states are denoted as $D_{obs}$; $R_{obs}$; $S_{obs}$. These observations are then applied to the network, and candidate (latent) diseases are ranked by their posteriors. That is, candidate diseases are ranked $D=\{D_1; D_2; ::: ; D_N\}$ such that $$P(D_i|D_{obs},R_{obs},S_{obs}) \geq P(D_{i+1}|D_{obs},R_{obs},S_{obs}), \forall i$$

This ranked list of diseases is then used to construct a diagnosis differential, a ranked list of diseases that should be tested for. This can be done in many ways, such as simply choosing the top N most likely diseases, or grading diseases in terms of cruelty to the patient and returning the top N for each cruelty grading. Regardless of how these diseases are ranked, the posterior ranking is the primitive ingredient of such differentials.

This approach correctly identifies the most likely diseases given the evidence. However, this is not necessarily what a doctor does when diagnosing a patient A doctor seeks to diagnose the disease which they believe to be the underlying cause of the presented evidence. In certain cases, the most likely disease given the evidence does not correspond to the underlying cause of the evidence. If the task of diagnosis is to determine the disease which should be treated in order to reduce or remove the presented symptoms, then outputting the most likely disease will in some cases systematically return the wrong ordering of candidate diseases to treat The three-layer CDMs as shown in FIG. 3 have a richer probabilistic structure than the two layer BN20 networks, which model only diseases and symptoms, and make unphysical assumptions such as disease priors being independent. Whilst this additional structure makes these newer models far more accurate than their predecessors, unobserved risk factors result in confounding between diseases, leading to spurious conclusions being drawn if one relies solely on observational statistics (see below).

Confounding: Latent risk factors allow for back-door paths between diseases (e.g. the thick edges in FIG. 3.). This can lead to diseases that have little or nothing to do with the presented symptoms being ranked highly in the differential due to their large posterior correlation with the symptoms through backdoor paths.

In the example DAG depicted in FIG. 3, consider the case where $s_2$; $s_4$; $s_5$=true and all other symptoms are un-evidenced, that is=false. Disease $D_2$ is a parent of all of the evidenced symptoms and could constitute the most likely cause of the underlying symptoms (depending on the details of the model). Disease $D_1$ is a parent of $S_2$ only—it cannot constitute a causal explanation for symptoms $S_4$ and $S_5$, whereas disease $D_K$ is a parent of none of the evidenced symptoms. Clearly, $D_K$ should be disregarded as it cannot possibly be a cause of the symptoms. However its posterior can be very high due to the back-door paths that it shares with $D_i$ and $D_2$.

Furthermore, if diseases like $D_1$ and $D_2$ are rare diseases such as cancer, with small priors and relatively small posteriors, $D_K$ can have a large enough posterior (or even prior) to make it impossible to discern rare but relevant diseases like $D_1$; $D_2$ from common, irrelevant diseases like $D_K$. Likewise the posterior weight of $D_1$ derives from a mixture of causative correlations with $S_2$ and backdoor correlations from sharing multiple risk-factor parents with $D_2$. Typically, it would be unlikely that $D_1$ is a good candidate disease for diagnosis, but it is simple to construct scenarios whereby $p(D_1|\varepsilon) \geq p(D_2|\varepsilon)$.

Counterfactual Ranking

In an embodiment, the counterfactual measure proposed—will be termed expected disablement—and is designed to rank diseases based on how well they explain the symptoms presented. As there are often multiple underlying diseases, it is too stringent to ask that all reported positive symptoms would disappear if it were not for a single disease (for example, if this disease is not a parent of one of these symptoms, the probability of disablement evaluates to 0). On the other hand, disease explanations that can explain as many symptoms as possible are favoured. To accommodate these two characteristics, the proposed measure takes the form of an expectation value.

Definition 3 (Expected disablement). The expected disablement of a disease $D_k$ with respect to evidence £ is the number of "on" symptoms would be expected to be switched off if there was an intervention to 'cure' $D_k$, given ε

$$\mathbb{E}_D(D_k, \mathcal{E}) = \sum_{S \subseteq S_+} |S_+ - S| p(S^*_{D_k=0} = 0 \mid \mathcal{E})$$

Where $S_+ = \{s \in S_{obs} \text{ s.t. } s=1\}$, $S_- = \{s \in S_{obs} \text{ s.t. } s=0\}$ and $\mathcal{E} = \{S_{obs}, D_{obs}, R_{obs}\}$. Here for notational connivance a superscript * is added to denote the counterfactual variable.

The expected disablement has three incredibly desirable properties that, mark it out as an important diagnostic measure.

Theorem 1 (Expected disablement decomposition). The expected disablement $\mathbb{E}_D(D_k; \mathcal{E})$ can be written as $$\sum_{S \subseteq S_+} |S_+ - S| p(S^*_{D_k=0} = 0 \mid D_k = 1, \mathcal{E}) p(D_k = 1 \mid \mathcal{E})$$

By Theorem 1, the expected disablement is an expectation value over the set of positively evidenced symptoms that are children of a given node, weighted by the 'causal effect' of $D_k$ on its children, and posterior of the disease given the evidence. It thus has the following three desirable properties.

1. Diseases with low posteriors are ranked low $$\lim_{P(D_k=1,\mathcal{E}) \mapsto 0} \mathbb{E}_D(D_k, \mathcal{E}) = 0$$

2. Diseases that explain many symptoms are ranked higher than diseases that explain fewer symptoms:

$$\lim_{S_+ \cap Ch(D_k) \mapsto \emptyset} \mathbb{E}_D(D_k, \mathcal{E}) = 0 \text{ and } \mathbb{E}_D(D_k, \mathcal{E}) \leq S_+ \cap Ch(D_k)$$

3. Diseases with low 'causal effect' on the symptoms are ranked low:

$$P(S_{D_k=0}^* = 0 \mid \mathcal{E}, D_k=1, \varepsilon) = 0 \Rightarrow \mathbb{E}D(D_k, \varepsilon) = 0$$

where $S = \{s \in S_+ \text{ s.t. } s \in Ch(D_k)\} S = fs$

The Causal approx of expected disablement:

$$\sum_{d_k} p(d_k \mid \mathcal{E}) |S - S_+| p(S \mid do(D_k = d_k))$$

this can be calculated without needing to know the functions

Next noisy-or models, a specific class of SCMs for Bernoulli variables that are widely employed as clinical diagnostic models, are defined. The noisy-or assumption states that a variable Y is the Boolean OR of its parents $X_1, X_2, \ldots, X_n$, where the inclusion or exclusion of each causal parent in the OR function is decided by an independent probability or 'noise' term. The standard approach to defining noisy-or is to present the conditional independence constraints generated by the noisy-or assumption.

$$p(Y = 0 \mid X_1, \ldots, X_n) = \prod_{i=1}^{n} p(Y = 0 \mid \text{only } (X_i = 1))$$

where $p(Y=0 \mid \text{only}(X_i=1))$ is the probability that $Y=0$ conditioned on all of its (endogenous) parents being 'off' ($X_j=0$) except for X, alone. We denote $p(Y=0 \mid \text{only}(X_i=1)) = \lambda_{Xi,Y}$ by convention.

The utility of this assumption is that it reduces the number of parameters needed to specify a noisy-or network to O(N) where N is the number of directed edges in the network. All that is needed to specify a noisy-or network are the single variable marginals $p(X_1=1)$ and, for each directed edge $X_i \to Y_j$, a single $\lambda_{Xi,Yj}$. For this reason, noisy-or has been a standard assumption in Bayesian diagnostic networks, which are typically large and densely connected and so could not be efficiently learned and stored without additional assumptions on the conditional probabilities. The noisy-or assumption for SCMs is now defined.

Definition 4 (Noisy-OR SCM). A Noisy-OR network is an SCM of Bernoulli variables, where for any variable Y with parents $Pa(Y) = \{X_1; \ldots; X_N\}$ the following conditions hold 1. Y is the logical OR of its parents, where for each parent X, there is a Bernoulli variable $U_i$ whose state determines whether the parent is included in the OR function, or if it is ignored $$y = \bigvee_{i=1}^{N} (x_i \wedge \bar{u}_i)$$

i.e. $Y=1$ if any parent is on, $x_i=1$, and is not ignored, $u_i=0$ ($\bar{u}_i = 1$ where 'bar' denotes the negation of $u_i$).

2. The probability of ignoring the state of a given parent variable is independent of whether any of the other parents have been ignored $$P(u_1, u_2, \ldots, u_N) \prod_{i=1}^{N} P(u_i)$$

3. For every node Y their is a parent 'leak node' $L_Y$ that is singly connected to Y and is always 'on', with a probability of ignoring given by $\lambda_{L_Y}$ The inclusion of assumption 3 is a convention (a leak node is just a parent L for which $p(L=1)=1$). The leak node represents the probability that $Y=1$, even if $X_i=0 \forall X_i \in Pa(Y)$. For example, the leak nodes allow the situation that a disease spontaneously occurs to be modelled, even if all risk factors that are modelled are absent, or that a symptom occurs but none of the diseases that are modelled have caused it Let us briefly consider the physical justification for the noisy-or assumption in modelling disease/symptom relationships, given Definition 4.

First, consider the assumption (1), that the generative function is a Boolean OR. This is equivalent to assuming that diseases or risk-factors never 'destructively interfere'. If $D_1$ is activating symptom S, and so is $D_2$, then this joint activation never cancels out to yield $S=F$. If two diseases are both activating a symptom, then the symptom is activated. Assumption 2 is also well justified in the clinical context. It states that a given disease (if present) has a fixed likelihood of activating a symptom, independent of the presence or absence of any other disease.

The above Noisy-OR assumptions allow great simplification of the model complexity, but also are fairly representative of how diseases/symptoms are expected to respond to their parent risk factors/diseases. For example, a symptom will be present if one parent disease, or another parent disease, is present. Furthermore, it is reasonable to expect that the probability that a symptom does not manifest, even if a parent disease is present, is (typically) independent of whether or not another disease is present Noisy-OR models are simple to learn from observational statistics. The latent priors, along with the single-variable priors, constitute all of the parameters needed to specify a Noisy-OR model. The following standard notation is used for the latent variable probabilities.

$$p(u_{X_i,Y_j} = 0) = \lambda_{X_i,Y_j} \quad (4)$$

Given the conditional probability distributions for single parent-child pairs, determining these latent priors (and hence fitting a Noisy-OR model) is a computationally simple task.

Theorem 2 (Learning Noisy-OR models). Lambdas can be calculated from pairwise conditional probability tables as $$\lambda_{X_i,Y_j} = \frac{p(Y_j = 0 \mid X_i = 1)}{p(Y_j = 0 \mid X_i = 0)} \quad (5)$$

As Noisy-OR models can be learned from single and two-variable statistics alone, they are particularly appealing for learning diagnostic models from epidemiological data, which usually comes in the form of double-blind studies involving small sets of variables.

As noisy-or models are typically presented as Bayesian networks, the above definition of noisy-or is non-standard. Below it is shown that the SCM definition yields the Bayesian network definition, (3).

Theorem 3 (Noisy-or CPT). The conditional probability distribution of a child Y given its parents $\{X_1, \ldots, X_n\}$ and obeying Definition 14 is given by $$p(Y = 0 \mid X_1 = x_1, \ldots, X_n = x_n) = \prod_{i=1}^{n} \lambda_{X_i,Y}^{x_i}$$

Proof. For Y=0, the negation of $\bar{y}$, denoted y, is given by $$\bar{y} = \neg \left( \bigvee_{i=1}^{N} (x_i \wedge \bar{u}_i) \right) = \bigwedge_{i=1}^{N} (\bar{x}_i \vee u_i)$$

The CPT is calculated from the structural equations by marginalizing over the latents. i.e. all latent states that yield Y=0 are summed over. Equivalently, it is possible to marginalize over all exogenous latent states multiplied by the above Boolean function, which is 1 if the condition Y=0 is met, and 0 otherwise.

$$p(Y = 0 \mid X_1 = x_1, \ldots, X_n = x_n) = \sum_{u_Y} \bigwedge_{i=1}^{N} (\bar{x}_i \vee u_i) p(u_Y)$$

$$= \sum_{u_{X_i,Y}} \prod_{X_i} (\bar{x}_i \vee u_i) \prod_{U_{X_i,Y}} p(u_{X_i,Y})$$

$$= \prod_{X_i} \sum_{u_{X_i,Y}} p(u_{X_i,Y})(\bar{x}_i \vee u_i)$$

$$= \prod_{X_i} [p(u_{X_i,Y} = 1) + p(u_{X_i,Y} = 0)\bar{x}_i]$$

$$= \prod_{X_i} [\lambda_{X_i,Y} + (1 - \lambda_{X_i,Y})\bar{x}_i]$$

$$= \prod_{X_i} \lambda_{X_i,Y}^{x_i}$$

This is identical to the noisy-or cpt (3).

Next, the expected disablement for Noisy-OR models will be derived. Above, there is a discussion of Pearl's algorithmic procedure for computing the probability of arbitrary counterfactuals.

The first step of this procedure, updating the distribution over latents and storing the resulting probabilities, requires a large amount of computational resources and memory. As this step has to be repeated for every new counterfactual query, the computational overheads can be quite costly. To overcome this, a twin network can be used.

Twin Networks: Twin networks are constructed by taking two copies of the original PGM (e.g. SCM), one to represent real variables and another to represent their counterfactual states. The two copies are linked by sharing exogenous latent variables (in the case of noisy-or, these are the noise terms $u_1$) between corresponding nodes. The counterfactual is then computed by applying a do-operation on the counterfactual graph and using belief propagation on the resulting model.

The construction of the twin network is illustrated in FIGS. 4 and 5.

FIG. 4 shows a simple example. FIG. 4[A] shows a structural causal model for two observed variables X, Y and their exogenous latents $u_X, u_Y$. FIG. 4 [B] illustrates the construction of the twin network, with X*,Y* representing the counterfactual states of X,Y. FIG. 4[C] shows the twin network under a hypothetical intervention setting do(X*=F). The counterfactual P(Y*|Y,do(X*=F)) is calculated from [C] using standard belief propagation.

FIG. 5 shows another example of how a twin network is formed. FIG. 5[A] shows the original PGM/SCM. In this example, the PGM has a directed acyclic graph structure, and comprises a feed-forward, three layer network. The top layer nodes represent risk factors $R_1 \ldots R_N$. The second layer nodes represent diseases $D_1 \ldots D_M$. The third layer nodes represent symptoms. This model assumes no directed edges between nodes belonging to the same layer.

To construct the twin network, first the SCM as shown in FIG. 5[A] is copied so that there are two networks as shown in FIG. 5[B]. In FIG. 5[B] the network on the left will encode the real evidence in a counterfactual query. This network is referred to as the 'real' graph.

The network on the right in FIG. 5[B] will take the hypothetical interventions and will yield the hypothetical observations. This network is referred to as the 'hypothetical' graph.

Pairs of copied variables are referred to as dual nodes. The nodes on the hypothetical graph denoted X* where X is the corresponding 'dual' node on the real graph. For example, in FIG. 5[B] $R_1$ and $R^*_1$ are dual nodes. Also, $D_1$ and $D^*_1$ are dual nodes.

The twin network of FIG. 5 [B] is constructed such that each node on the real graph shares its exogenous latent with its dual node, so $u^*_{Xi}=u_{Xi}$. These shared exogenous latents are depicted as dashed lines in FIG. 5 [B] to [E].

A disease node is selected in the hypothetical graph to perform the intervention on. In the example shown in FIG. 5 [B], the disease node $D^*_2$ is selected in the hypothetical graph to perform the intervention on.

Darker shaded circles indicate observations, whereas lighter shaded circles indicate interventions.

Applying the do-operation do($D^*$=0) to the hypothetical disease node $D^*$ cuts any directed edges doing into $D^*$ and fixes $D^*$=0, as shown in FIG. 5 [D] below.

Once the hypothetical intervention has been applied, it is possible to greatly simplify the twin network graph structure via node merging. In SCM's a node is fully determined given an instantation of all of its parents and its exogenous latent. Hence, if two nodes have identical exogenous latents and parents, they are copies of each other and can be merged into a single node.

By convention, when dual nodes are merged there is a mapping $X^* \to X$ (dropping the asterisk). Dual nodes which share no ancestors that have been intervened upon can therefore be merged.

As interventions are not performed on the risk factor nodes, all ($R_i$, $R^*_i$) are merged (as shown in FIG. 5[D]. Note that for the sake of clarity the exogenous latents for risk factors are not depicted in FIG. 5 [C]-[D].

Alternatively, because the risk factor nodes ($R_i$, $R^*_i$) are not children of the intervention node ($D^*_2$ which is a disease node), the risk factor nodes ($R_i$, $R^*_i$) can be merged before applying the intervention, as shown in FIG. 5 [C].

Following this, all corresponding real/hypothetical disease nodes that have no interventions ancestors can be merged, as their latents and parents are identical (shown in FIG. 5[D]).

Finally, any symptoms that are not children of the disease that has been intervened upon can be merged, as again their latent and all of their parent variables are identical. In FIG. 5[D], only $S_1$ has any evidence applied to it. As the symptoms are at the bottom of the graph, if they are un-evidenced they can be removed (this is true for all graphical models when doing inference). So only $S_1$ and its dual $S_1^*$ remain.

The resulting twin network is depicted in FIG. 5 [E]. In FIG. 5[E], $D_M$ is shown as being greyed out. This is because it is not a parent of any of the symptoms. Thus, just like the symptoms that were removed as described above, it is at the bottom of the network and unevidenced. So it is superfluous to the task of inference and hence can be removed it. This is the case for all nodes that are not parents pf the symptoms.

Counterfactuals are then computed from the posteriors on this twin network. For example in FIG. 5[E], the counterfactual $p(S_{1D_1=0}=0|S_1=1)$ is given by $p(S^*_1=0|S_1=0, D^*_2=0)$.

This approach massively amortizes the standard inference cost of calculating counterfactuals by abduction, action and prediction, which would otherwise be intractable for large clinical diagnostic models (CDMs).

Noisy-or Twin Networks

A noisy-or SCM (for example that described above) can be used to derive the conditional probability tables (CPTs) on the twin network. The only CPTs that differ from the original noisy-or SCM are those for unmerged dual symptom nodes (i.e. children of the intervention node DK). In one embodiment, the diagnostic twin network is feed-forward and as such the disease layer forms a Markov blanket for the symptoms layer, d-separating dual symptom pairs from each other. As a result, the CPTs for dual symptoms and their parent diseases alone are derived.

Lemma 1: For a given symptom S and its hypothetical dual $S^*$, with parent diseases D and under the hypothetical intervention do($D^*k$=0), the joint conditional distribution on the twin network is given by $$p(s, s^* | \mathcal{D}_{\setminus k}, D_k, do(D_k^* = 0)) =$$

$$\begin{cases} p(s = 0 | \mathcal{D}) & \text{if } s = s^* = 0 \\ 0 & \text{if } s = 0, s^* = 1 \\ \left(\frac{1}{\lambda_{D_k, S}} - 1\right) p(s = 0 | \mathcal{D}_{\setminus k}, D_k = 1)\delta(d_k - 1) & \text{if } s = 1, s^* = 0 \\ p(s = 1 | \mathcal{D}_{\setminus k}, D_k = 1)/\lambda_{D_k, S} & \text{if } s = 1, s^* = 1 \end{cases}$$

where $\delta(d_k-1)=1$ if $D_k=1$ else 0, and $D=D_{\setminus k} \cup D_k$, i.e. $D_{\setminus k}$ is the set of diseases that are not intervened on.

The proof for the above Lemma can be found in Annex 1.

When comparing counterfactual and posterior diagnosis, improved diagnostic accuracy should not come at the expense of greater computational cost. To overcome this issue, a closed form expression is now derived for the expected disablement in Noisy-OR diagnostic networks that only requires knowledge of the observational statistics, as is the case for posterior ranking.

Lemma 1 reduces the counterfactual query to an observational query on the original noisy-or network, with some simple adjustments to the conditional probabilities. We want to evaluate the expected disablement of the hypothetical intervention do($D^*_k$=0), which is defined as $$\mathbb{E}_{D_K, \mathcal{E}} := \sum_{S'} |S_+ - S'_+| p(S'|\mathcal{E}, do(D_k = 0))$$

where the sum enumerates over all possible the hypothetical symptom states that are consistent with the real evidence E and the intervention do($D_k$=0). $S_\pm$ denote the positive/negative symptoms in the evidence set S. The intervention do($D_k$=0) can never switch on symptoms, so one need only enumerate over hypothetical symptoms states where $S_+ \subseteq S_+$ as these are the only counterfactual states with non-zero weight. From this it also follows that for all $s \in S_- \Rightarrow s^* \in S'_-$. Expressing the counterfactual (17) as a query on the twin network, the positive/negative symptoms on the hypothetical graph are denoted as $S^*_\pm$. The counterfactual posterior in (17) is represented on the twin network as $$p(S_+^*, S_-^* | \mathcal{E}, do(D_k^*=0)) = p(S_+^*, S_-^* | S_+, S_-, R_{obs}=r, do(D_k^*=0))$$

Theorem 4 (Noisy-OR expected disablement). The expected disablement of intervention $\hat{D}_k^*$=0 can be written $$\mathbb{E}_{\hat{D}_k} = \frac{1}{p(S_+, S_-)} \sum_{X \in S_+} (-1)^{|S_+|-|X|} \Lambda_{X,k} \sum_{s \in X} \frac{1-\lambda_{sk}}{\lambda_{sk}} \times$$

$$P\left(S_- = 0, X_{\hat{D}_k=0} = 0, D_k = 1 | \mathcal{R}_{obs}\right)$$

-continued where $X_{\hat{D}_k=0}$ means $s_{\hat{D}_k=0} \forall s \in X$ and $\Lambda_{X,k} = \prod_{s \in X} \lambda_{k,s}$.

Alternatively, the theorem can be expressed as follows:

For the noisy-or networks described above, the expected disablement of disease $D_k$ is given by $$\mathbb{E}_{D_k,\varepsilon} = \frac{1}{p(S_+, S_- | \mathcal{R}_{abs} = r)} \sum_{C = S_- \wedge Ch(D_k)} |C| p(C = 0,$$

$$S_\pm \backslash C | D_k = 1, \mathcal{R}_{abs} = r) p(D_k = 1 | \mathcal{R}_{abs} = r) \frac{\prod_{S \in C}(\lambda_{D_k,s} - 1)}{\prod_{S \in S_+} \lambda_{D_k,s}}$$

where $S_\pm \backslash C$ denotes $S_- = 0$, $S_+ \backslash C = 1$.

The proof for the above equation can be found in Annex 1.

Note that as all common causes in the three-layer Noisy-OR diagnostic network are observed, the probability $P(S_-=0, X_{\hat{D}_k}=0, D_k=1|R_{obs})$ can be identified in terms of purely observational probabilities via the Backdoor criterion (Pearl, J. 2009. Causality (2nd edition). Cambridge University Press).

Experimentally Comparing Counterfactual and Posterior Diagnosis

Existing algorithms fail to incorporate causal knowledge in the diagnostic process. The counterfactual diagnosis measure captures this causal information.

To evaluate the effectiveness of our counterfactual diagnostic measure, a comparison of the diagnostic precision for the described CDM using posterior ranking and expected disablement ranking of diseases is performed.

The following definition of diagnosis is taken: the determination of the diseases that are most likely to be causing the observed symptoms. We devise a minimal criteria for desirable diagnostic measures to reflect this definition; i) $M(Dk) \to 0$ smoothly as $P(Dk=T|E) \to 0$ (consistency), ii) $M(Dk)=0$ for diseases that are not ancestors of any positive symptoms and therefore cannot constitute causal explanations for and observed symptoms (causality), and iii) diseases that explain a greater number of positive symptoms should be ranked highly (simplicity). From this criteria counterfactual diagnostic measure is selected as the expected disablement E(Dk), $$\mathbb{E}(D_K, \mathcal{E}) := \sum_{S'} |S_+ - S'_+| p(S'|\mathcal{E}, do(D_k = F))$$

where E is the total evidence state, S+ denotes the set of positive symptom evidence, S' is a counterfactual symptom state with S'+={S∈S'|S=T}. The expected disablement is the number of symptoms that one would expect to nullify, had one intervened to cure disease $D_k$.

The performance of the diagnostic measure are tested against a set of 600 clinical vignettes. These vignettes are produced by a panel of expert medical professionals, and contain a single ground-truth disease, a collection of symptoms and risk factors, and basic demographic information such as age and gender.

The symptom and risk factor evidence are selected by the expert panel to represent the evidence that could typically be presented to a doctor by a patient who has the vignette disease. Approximately half of the vignettes attempt to model rare diseases, whereas the other half model diseases of high incidence. The task of the diagnostic algorithm is to return a differential of N diseases ranked in terms of their likelihood given the evidence on each vignette. The same diagnostic model is used for evaluating each measure. This model is a Noisy-OR model containing 1300 nodes, constructed using expert knowledge and epidemiological data (Razzaki, S.; Baker, A.; Perov, Y.; Middleton, K.; Baxter, J.; Mullarkey, D.; Sangar, D.; Taliercio, M.; Butt, M.; Majeed, A.; et al. 2018. A comparative study of artificial intelligence and human doctors for the purpose of triage and diagnosis. arXiv preprint arXiv:1806.10698.).

As a simple test of diagnostic accuracy, the accuracy of the top-N differential for posterior and counterfactual ranking were compared, with respect to the ground truth disease. The accuracy is defined as the probability that the ground truth disease is within a differential of size N, for N=1; : : : ; 20.

Given a differential $H_M^{(N)} = \{D_1, D_2, \ldots, D_N\}$ where $M(D_i)$ $M(D_{i+1})$ where $M(\cdot)$ is the chosen ranking measure, the accuracy of the ranking is simply calculated as the probability of the inclusion of the ground-truth disease $H_M^{(N)}$.

Figure 6:
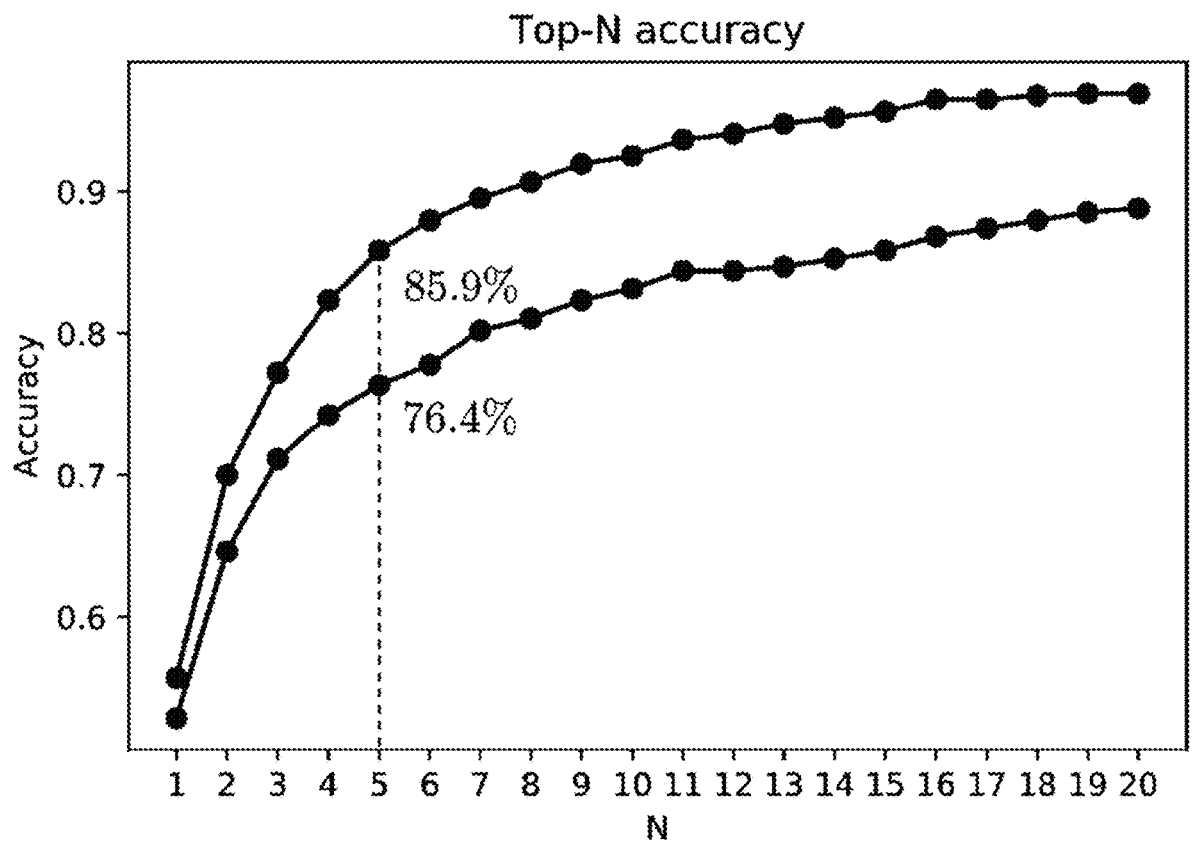
FIG. 6 is a plot showing a comparison of results for counterfactual ranking against posterior ranking.

FIG. 6 shows the top-N accuracy of a Noisy-OR test model as calculated on 750 vignettes. As half of vignettes cover rare diseases, for which the ground truth disease should typically not be at the top of the ranking, rankings of N are focused upon.

The top line represents the accuracy of differentials of size N for the counterfactual ranking, given by $\mathbb{E}_D(D; \varepsilon)$, and likewise for the lower line and posterior ranking P(D; S).

In this regime, using the counterfactual ranking approximately halves the error rate of the diagnosis compared to posterior ranking.

The two diagnostic measures are compared to the diagnoses of human doctors. For each case-card a diagnosis is gathered from four expert doctors, who are given each case card with the model disease masked and asked to provide a list of possible model diseases ranked from very likely to unlikely. All diseases that at least one doctor flagged as likely (P(D=T|ε)≥0.3) are combined, and this is used as the 'ground truth' optimal diagnosis, as it represents the outcome of a 4th opinion expert consultation. For each doctor their precision is measured as the average fraction of the ground truth diseases for each case card that they predicted as likely, and likewise for the clinical diagnostic model (CDM) with M(Dk, E)≥0.3. Whilst this approach has an inherent bias towards doctors, as their assessment define the ground truth, it is necessary in order to model the inherent diagnostic uncertainty. Results are presented in the table of FIG. 7.

In general, the single limiting factor of counterfactual diagnosis is the requirement that the full structural causal model be known in order to compute the expected disablement. Indeed, in purely observational graphical diagnostic models, where the generative functions are unknown, the expected disablement may not be identifiable. However, there is a halfway house between posterior and full counterfactual diagnosis, given by interventional queries from the second level of the causal hierarchy. A simplified version of the quantity envisaged is as follows:

$$|P(S_{D=0}=0)-P(S=0)|P(D=1|S=1)$$

As all common causes in a three-layer Noisy-OR diagnostic network are observed, the above quantity can be identified in terms of purely observational probabilities via the Backdoor criterion, assuming the graphical structure of the network is known.

The above counterfactual diagnosis method can be used with any of the known approximate inference techniques, for example, Importance Sampling. The above inference technique can also be used with inference techniques described in Douglas et al "A Universal Marginalizer for Amortized Inference in Generative Models" arXiv: 1711.00695v1 [cs.LG] 2 Nov. 2017.

Figure 8:
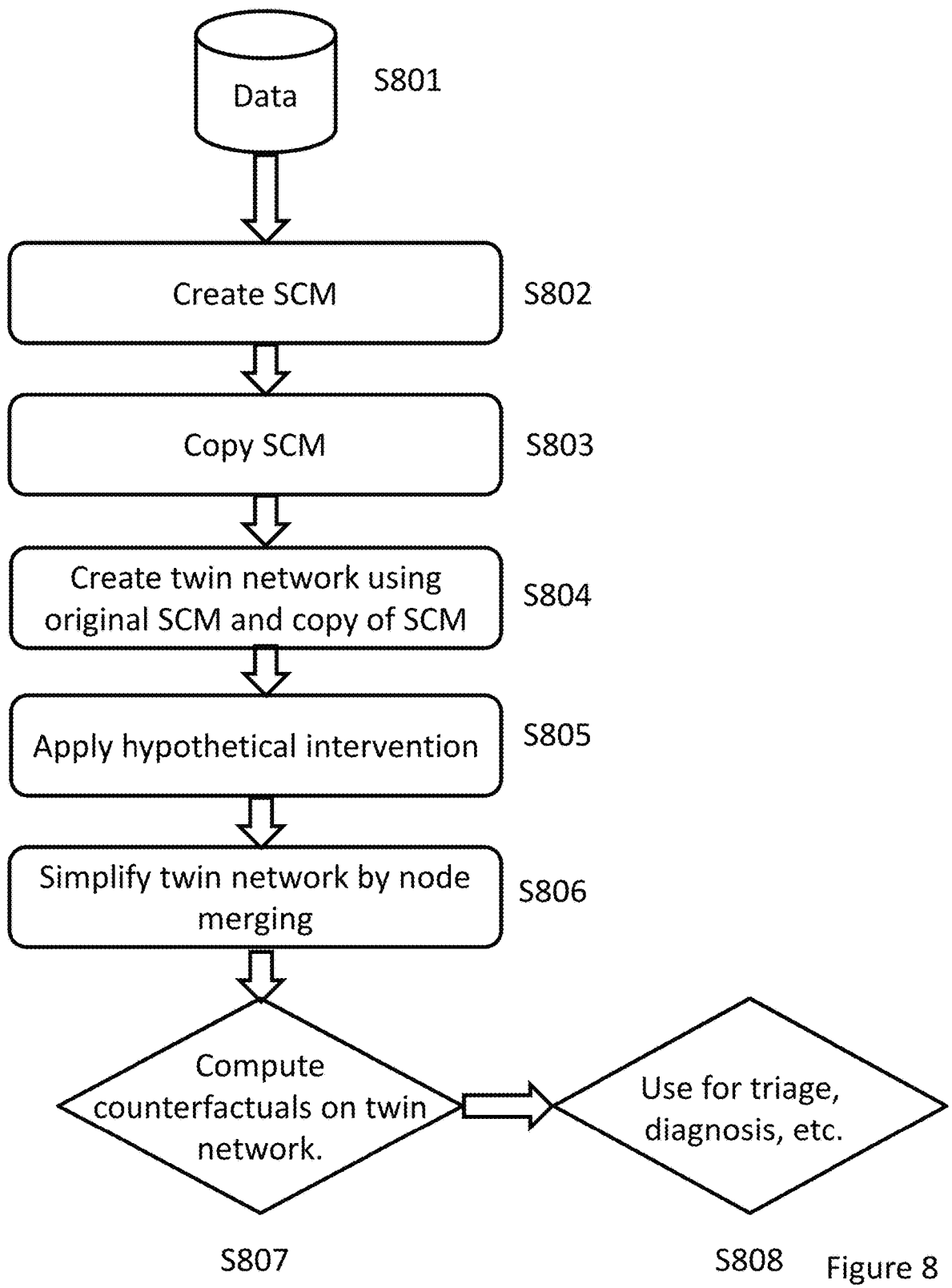
FIG. 8 is a flow chart depicting a method in accordance with an embodiment.

FIG. 8 is a flow chart depicting an embodiment of the counterfactual diagnosis method. In step S801, data is received. This data can be epidemiological data, expert knowledge, data from research studies or other data. A PGM, or SCM, is created (S802). The SCM may be a noisy-or SCM. A copy of the SCM is made in S803.

In step S804, the twin network is created using the original SCM from S802 and the copy from S803.

Once the twin model is created, the hypothetical intervention can be applied (S805). Next, the twin network can be simplified through merging nodes (S806).

The twin network can then be used in the computation of counterfactuals (S807).

In step S808, the resultant PGM is then used for triage, diagnosis etc. For, example, this can be as described with reference to FIG. 9.

Figure 9:
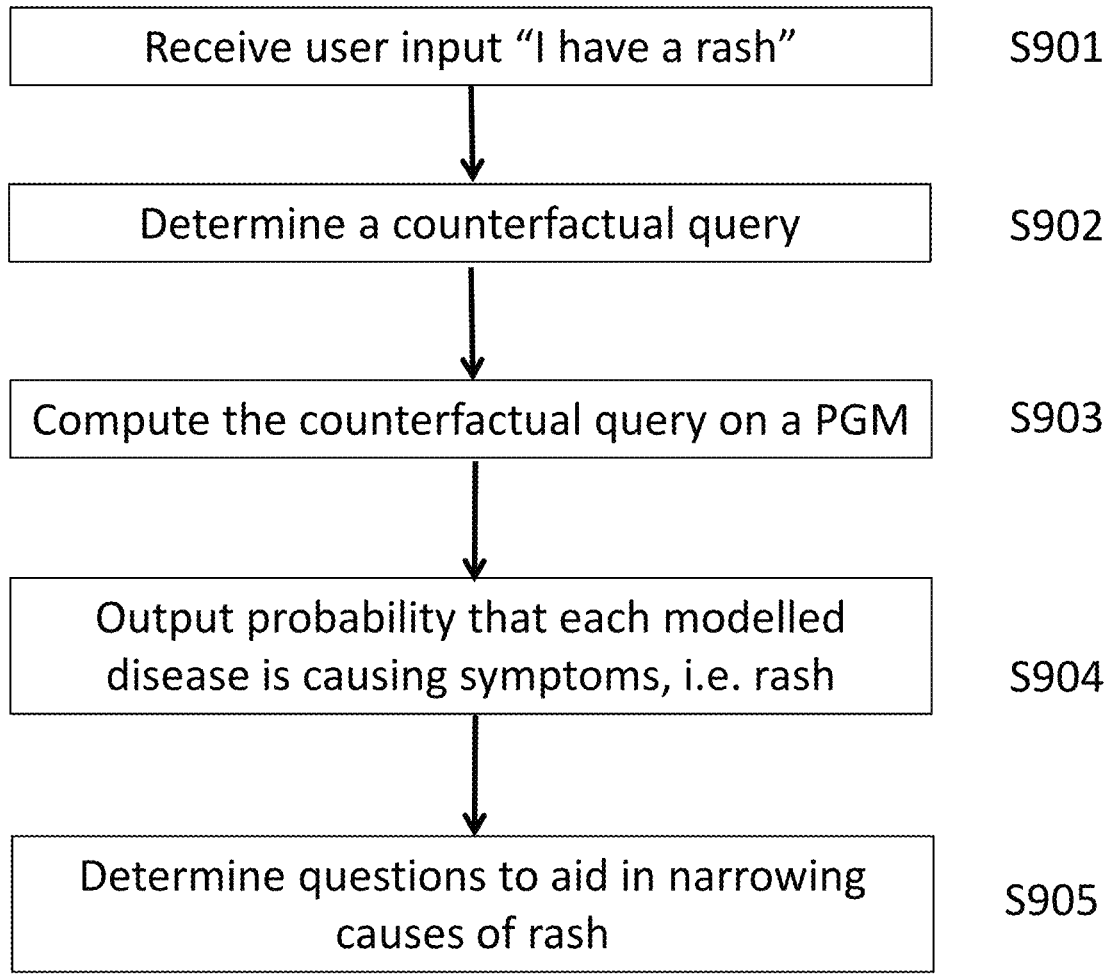
FIG. 9 is a flow chart showing a method in accordance with a further embodiment.

In step S901 of FIG. 9, the user inputs the phrase, for example, "I have a rash" into, for example, the mobile telephone of FIG. 1. This phrase is then passed to system and used to determine a counterfactual query (S902). The counterfactual query is then computed (S903) on the PGM through by identifying a node in the PGM that relates to the user's query. The PGM then outputs the probabilities that each modelled disease is causing the rash (S904).

The system may also determine further questions that will allow the possible causes for the user's symptoms to be narrowed (S905).

At least some of the described approaches include reasoning about causal responsibility (also referred to as causal attribution). A definition of causal responsibility is the probability that the occurrence of an effect, S, e.g. a symptom, was brought about by a target cause, D, e.g. a disease. Reasoning about causal responsibility utilizes a diagnostic measure M(D,$\varepsilon$) for ranking the likelihood (e.g. probability) that a disease D is causing a patient's symptoms given evidence $\varepsilon$. Criteria that should be satisfied by a desirable diagnostic measures include:

i) Consistency—the likelihood that a disease D is causing a patient's symptoms should be proportion to the posterior likelihood of that disease: M(D,$\varepsilon$)$\propto$P(D=T|$\varepsilon$).

ii) Causality—a disease that cannot cause any of the patent's symptoms cannot constitute a diagnosis: M(D, $\varepsilon$)=0.

iii) Simplicity—diseases that explain a greater number of the patient's symptoms should be more likely.

Consistency, causality and simplicity are also described above using alternative notation and terminology.

The justification for these criteria is as follows. Consistency states that the likelihood that a disease explains the patient's symptoms is proportional to the likelihood that the patient has the disease in the first place. Causality states that if there is no causal mechanism whereby disease D could have generated any of the patient's symptoms (directly or indirectly), then D cannot constitute causal explanation of the symptoms and should be disregarded. Simplicity incorporates the principle of Occam's razor—favouring simple diagnoses with few diseases that can explain many of the symptoms presented. The posterior satisfies consistency but violates causality and simplicity.

As previously described, counterfactual inference may be used to quantify the likelihood that a disease is causing a patient's symptoms. Such counterfactual inference may be used in determining diagnostic measures. These diagnostic measures utilizing counterfactual inference are referred to as counterfactual measures. An example of a counterfactual measure—expected disablement—has been described above. Several counterfactual measures are explained below including expected disablement, which is explained again for the sake of completeness, and other counterfactual measures. Each of the several counterfactual measures based on whether one or more symptoms would be expected to be present if a given one or more diseases were cured. The several counterfactual measures satisfy the criteria of consistency and causality described above. Expected disablement, generalized expected disablement, expected sufficiency, and generalized expected sufficiency also satisfy the criteria of simplicity described above. The several counterfactual measures are presented as examples, and it should be understand that they may be modified, combined or generalized in any suitable manner. A counterfactual measure may be a function of one or more of the several counterfactual measures described. A counterfactual measure may be a function of one or more of the several counterfactual measures described. For example, the counterfactual measure may be a multiple, fraction, logarithm, exponential, root or exponentiation of one of the several counterfactual measures. As other examples, the counterfactual measure may be a sum, weighted sum, average, or weighted average of a plurality of the several counterfactual measures or of functions thereof, e.g. a polynomial of a plurality of the counterfactual measures.

A counterfactual measure is the expected disablement of disease D, which is the expected number of symptoms that would no longer be present if the disease D was cured, e.g. the number of symptoms that would be expected to switch off if an intervention cured the disease D.

An equation for the expected disablement is:

$$\mathbb{E}_{dis}(D, \mathcal{E}) := \sum_{S'} |S_+ \setminus S'_+| P(S'|\mathcal{E}, do(D = F))$$

where $\varepsilon$ is the factual evidence and $S_+$ is the set of factual positively evidenced symptoms. The summation is calculated over all possible counterfactual symptom evidence states S' and $S_+'$ denotes the positively evidenced symptoms in the counterfactual symptom state. do(D=F) denotes the counterfactual intervention setting D$\rightarrow$F. $|S_+\setminus S_+'|$ denotes the cardinality of the set of symptoms that are present in the factual symptom evidence but are not present in the counterfactual symptom evidence.

The expected disablement derives from the notion of necessary cause, whereby D is a necessary cause of S if S=T if and only if D=T. The expected disablement captures how well disease D alone can explain the patient's symptoms as well as the likelihood that treating D alone will alleviate the patient's symptoms.

A proof that expected disablement satisfies the criteria of consistency, causality and simplicity is included in Annex 2.

Another counterfactual measure is the generalized expected disablement. The generalized expected disablement is a variation of the expected disablement. The generalized expected disablement is the expected number of symptoms that would not longer be present if a set of diseases, H, were cured, where $H=(D_1, D_2, \ldots, D_k)$, e.g. the number of symptoms that would be expected to switch off if an intervention cured the set of diseases H.

An equation for the generalized expected disablement is:

$$\mathbb{E}_{dis}(\mathcal{H}, \mathcal{E}) := \sum_{S'} |S_+ \setminus S'_+| P(S'|\mathcal{E}, do(\mathcal{H} = F))$$

Another counterfactual measure is the probability of nullification. The probability of nullification is the probability that curing a disease, $D_k$, would result in the patient having no symptoms given factual evidence, E. When the probability of nullification is used as a counterfactual measure, the assumption may be made that a patient has a single disease.

An equation for the probability of nullification is $$P_{null}(D_k, \mathcal{E}) := P(S_+^* = 0 | \varepsilon, do(D_k^* = 0))$$

where $S_+ = \{S_i \in \varepsilon \text{ s.t. } S_i = 1\}$.

The expected disablement, the generalized expected disablement and the probability of nullification are examples of counterfactual measures where the value of the counterfactual measure for one or more given diseases is based on whether one or more symptoms would not be expected to be present if those one or more given diseases were cured.

Another counterfactual measure is the expected sufficiency. The expected sufficiency of disease D is the number of positively evidenced symptoms that would be expected to persist, e.g. continue to be present, if other possible causes of the patient's symptoms cured, e.g. one or more interventions switched off all other possible causes of the patient's symptoms.

An equation for the expected sufficiency is:

$$\mathbb{E}_{suff}(D, \mathcal{E}) := \sum_{S'} |S'_+| P(S'|\mathcal{E}, do(\text{Pa}(S_+) \setminus D = F))$$

where the summation is over all possible counterfactual symptom evidence states S' and $S_+'$ denotes the positively evidenced symptoms in the counterfactual symptom state.

$\text{Pa}(S_+') \setminus D$ denotes the set of all direct causes of the set of positively evidenced symptoms excluding disease D, and $do(\text{Pa}(S_+) \setminus D = F)$ denotes the counterfactual intervention setting all $\text{Pa}(S_+ \setminus D) \rightarrow F$, e.g. curing all diseases other than disease D that could directly cause the set of positively evidence symptoms and/or removing all exogenous influences that could directly cause the set of positively evidenced symptoms. E denotes the set of all factual evidence. $|S_+'|$ denotes the cardinality of the set of present symptoms in the counterfactual symptom evidence.

The expected sufficiency derives from the notion of sufficient cause, whereby D is a sufficient cause of S if the presence of D can cause subsequent occurrence of S but, as S can have multiple causes, the presence of S does not imply the prior occurrence of D. Diseases may be sufficient causes of symptoms. By performing counterfactual interventions to remove other possible causes of the symptoms, e.g. diseases and/or exogenous influence, the only remaining cause is D and its effect as a sufficient cause is isolated. If it cannot be assumed that a disease is a sufficient cause of its symptoms then the use of expected disablement may be preferable.

A proof that expected sufficiency satisfies the criteria of consistency, causality and simplicity is included in Annex 2.

Expected sufficiency also satisfies a further desirable criteria of sufficiency. Sufficiency specifies that if it is possible that a disease $D_k$ is causing at least one symptom, then the measure should be strictly greater than 0. Sufficiency may be represented mathematically as the postulate:

$$\mathbb{E}_{suff}(D_i \wedge D_j, \varepsilon) > 0 \Rightarrow \mathbb{E}_{suff}(D_i, \varepsilon) > 0 \text{ and } \mathbb{E}_{suff}(D_j, \varepsilon) > 0$$

The proof that expected sufficiency satisfies the criteria of sufficiency is also included in Annex 2.

Another counterfactual measure is the generalized expected sufficiency. The generalized expected sufficiency is a variation of the expected sufficiency. The generalized expected disablement is the expected number of symptoms that would still be present, e.g. persist, if all possible causes of the symptoms other than a set of diseases, H, were cured, where $H=(D_1, D_2, \ldots, D_k)$, e.g. the number of symptoms that would be expected to remain if an intervention cured all diseases other than the set of diseases H and/or removing all exogenous influences that could directly cause the set of positively evidenced symptoms.

An equation for the generalized expected disablement is:

$$\sum_{S'} |S'_+| P(S'|\mathcal{E}, do(\text{Pa}(S_+) \setminus \mathcal{H} = F))$$

Another counterfactual measure is single disease sufficiency. The single disease sufficiency is the probability that all of the patient's symptoms would remain if every possible cause of the patient's other than a single disease $D_k$, e.g. the probability that all of the patients symptoms would persist if all other possible diseases that could directly cause the symptoms were cured and/or all exogenous factors that could directly cause the patient's symptoms were removed. When the single disease sufficiency is used as a counterfactual measure, the assumption may be made that a patient has a single disease.

An equation for the single disease sufficiency is:

$$P(S_+ = 1 | \varepsilon, do(\text{Pa}(S_+) \setminus D_k = F))$$

The expected sufficiency, the generalized expected sufficiency and the single disease sufficiency are examples of counterfactual measures where the value of the counterfactual measure for one or more given diseases is based on whether one or more symptoms would be present, e.g. persist or remain, if diseases that could cause the one or more symptoms other than the one or more given diseases were cured and/or exogenous factors that could cause the one or more diseases were removed.

The described counterfactual measures may be calculated using Noisy-Or networks of the type described above, e.g. in relation to FIG. 5.

Theorem 5: (Noisy-Or Expected Sufficiency and Expected Disablement) For Noisy-Or networks, the expected sufficiency and expected disablement of a disease $D_k$ may be calculated as:

$$\frac{\sum_{\mathcal{Z} \subseteq S_+} (-1)^{|\mathcal{Z}|} P(S_- = 0, \mathcal{Z} = 0, D_k = 1 | \mathcal{R}) \tau(k, \mathcal{Z})}{P(S_\pm | \mathcal{R})}$$

where for the expected sufficiency:

$$\tau(k, \mathcal{Z}) = \sum_{S \in \mathcal{Z}} \left(1 - \frac{1}{\lambda_{D_k, S}}\right)$$

and where for the expected disablement:
where $S_\pm$ denotes the positive and negative symptom evidence, R denotes the risk-factor evidence, and $\lambda_{D_k, S}$ is the noise parameter for $D_k$ and S. A proof of theorem 5 may be found in Annex 2.

Figure 10:
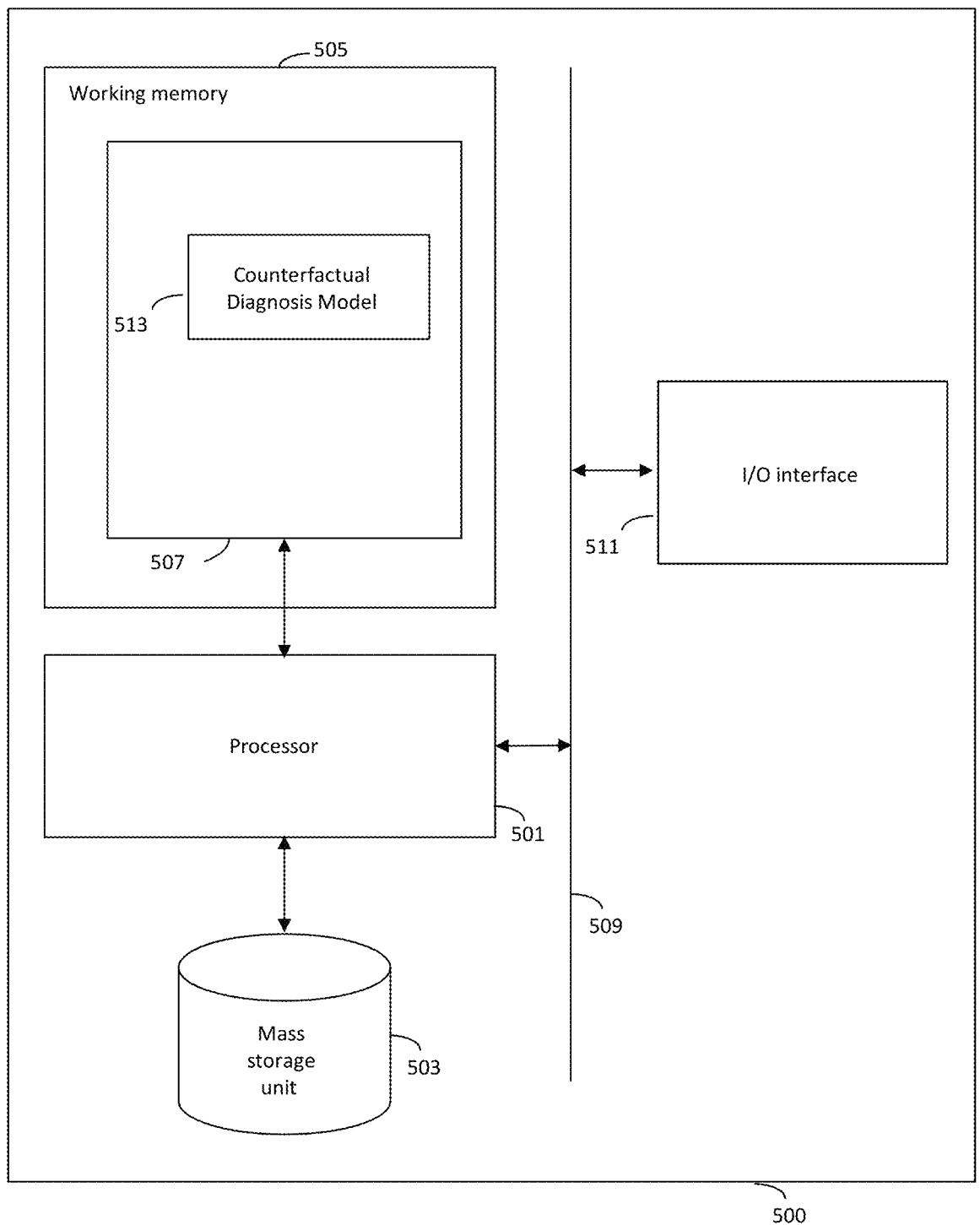
FIG. 10 is a schematic of a system in accordance with an embodiment.

While it will be appreciated that the above embodiments are applicable to any computing system, an example computing system is illustrated in FIG. 10, which provides means capable of putting an embodiment, as described herein, into effect. As illustrated, the computing system 500 comprises a processor 501 coupled to a mass storage unit 503 and accessing a working memory 505. As illustrated, a counterfactual diagnosis model 513 is represented as software products stored in working memory 505. However, it will be appreciated that elements of the counterfactual diagnosis model 513, may, for convenience, be stored in the mass storage unit 503. Depending on the use, the counterfactual diagnosis model 513 may be used with a chatbot, to provide a response to a user question that requires the survival analysis model.

Usual procedures for the loading of software into memory and the storage of data in the mass storage unit 503 apply. The processor 501 also accesses, via bus 509, an input/output interface 511 that is configured to receive data from and output data to an external system (e.g. an external network or a user input or output device). The input/output interface 511 may be a single component or may be divided into a separate input interface and a separate output interface.

Thus, execution of the counterfactual diagnosis model 513 by the processor 501 will cause embodiments as described herein to be implemented.

The counterfactual diagnosis model 513 can be embedded in original equipment, or can be provided, as a whole or in part, after manufacture. For instance, the counterfactual diagnosis model 513 can be introduced, as a whole, as a computer program product, which may be in the form of a download, or to be introduced via a computer program storage medium, such as an optical disk. Alternatively, modifications to existing causal discovery model software can be made by an update, or plug-in, to provide features of the above described embodiment The computing system 500 may be an end-user system that receives inputs from a user (e.g. via a keyboard) and retrieves a response to a query using counterfactual diagnosis model 513 adapted to produce the user query in a suitable form. Alternatively, the system may be a server that receives input over a network and determines a response. Either way, the use of the counterfactual diagnosis model 513 may be used to determine appropriate responses to user queries, as discussed with regard to FIG. 1.

Further Results

Experiments comparing the expected disablement and expected sufficiency to posterior inference using the models outlined in the previous section are outlined. The test set includes a set of clinical vignettes and a cohort of doctors is introduced. Then, the algorithms are evaluated across several diagnostic tasks.

One approach to validating diagnostic algorithms is to use electronic health records (EHRs) [8-12]. A key limitation of this approach is the difficulty in defining the ground truth diagnosis, where diagnostic errors result in mislabeled data. This problem is particularly pronounced for differential diagnoses because of the large number of candidate diseases and hence di-agnostic labels, incomplete or inaccurate recording of case data, high diagnostic uncertainty and ambiguity, and biases such as the training and experience of the clinician who performed the diagnosis.

A standard method for assessing doctors is through the examination of simulated diagnostic cases, e.g. clinical vignettes. A clinical vignette simulates a typical patient's presentation of a disease, containing a non-exhaustive list of evidence including symptoms, medical history, and basic demographic information such as age and birth gender. This approach is often more robust to errors and biases than real data sets such as EHRs, as the task of simulating a disease given its known properties is simpler than performing a differential diagnosis, and has been found to be effective for evaluating human doctors and comparing the accuracy of doctors to symptom checker algorithms.

To assess the algorithms, a test set of 1671 clinical vignettes is used, where the test set is generated by a separate panel of doctors qualified at least to the level of general practitioner. The clinical vignettes are generated independently of the assumptions underlying the disease model. Where possible, symptoms and risk factors match those in the disease model. However, to avoid biasing the results, the vignettes include any additional clinical information as case notes, which are available to the doctors in the experiments. Each clinical vignette is authored by a single doctor and then verified by multiple doctors to ensure that it represents a realistic diagnostic case. For each vignette the true disease is masked and the algorithm returns a diagnosis in the form of a full ranking of all modelled diseases using the vignette evidence. The disease ranking is computed using the posterior for the associative algorithm, and the expected disablement or expected sufficiency for the counterfactual algorithms. Doctors provide an independent differential diagnosis in the form of a partially ranked list of candidate diseases.

An example of a clinical vignette is given below. As can be seen in the example below, the clinical vignette may include information pertaining to the medical concept, whether or not it is included in the disease model, and/or whether or not it is present in the patient. {
  age: 60,
  diseases: Carcinoid tumour
  duration: Months,
  gender: Male,
  initial input: I am suffering from facial flushing,
  risk factors: [
    {name: Dyslipidemia
    in model: True
    presence: present},
    {name: Essential hypertension
    in model: True
    presence: present},
    {name: Ex-smoker
    in model: True
    presence: present},
    {name: Family history of diabetes mellitus type 2
    in model: True
    presence: present},

```
[name: Family history of bowel cancer
  in model: True
  presence: present}
],
symptoms: [
  {name: Flushing
   in model: True
   presence: present},
  {name: Diarrhea
   in model: True
   presence: present},
  {name: Facial redness
   in model: False
   presence: present},
  {name: Flushing worse with exercise and stress
   in model: False
   presence: present},
  {name: Flushing triggered by alcohol, chocolate and
     bananas
   in model: False
   presence: present},
  {name: Fresh blood PR (hematochezia)
   in model: True
   presence: present},
  {name: Cramping Generalized Abdominal Pain
   in model: True
   presence: present},
  {name: Palpitations
   in model: True
   presence: not present},
  {name: Unintentional weight loss
   in model: True
   presence: not present},
  {name: Wheezing
   in model: True
   presence: not present}
],
}
```

In all experiments the counterfactual and associative algorithms use identical disease models to ensure that any difference in diagnostic accuracy is due to the ranking query used. The disease model used is a noisy-OR network as described above. The network is parameterized by a team of doctors and epidemiologists. The model is specified independently of the test set of vignettes. The prior probabilities of diseases and risk factors are obtained from epidemiological data, and conditional probabilities are obtained through elicitation from multiple independent medical sources and doctors. The expected disablement and expected sufficiency are calculated using Theorem 5.

A first experiment compares the diagnostic accuracy of ranking diseases using the posterior, expected disablement and expected sufficiency. For each of the 1671 vignettes the top-k ranked diseases are computed, with k=1, . . . , 20, and the top-k accuracy is calculated as fraction of the 1671 diagnostic vignettes where the true disease is present in the k-top ranking. The results are presented in FIG. 11. The expected disablement and expected sufficiency give almost identical accuracies for all k on our test set, and for the sake of clarity, the results are presented for the expected sufficiency alone.

Figure 11:
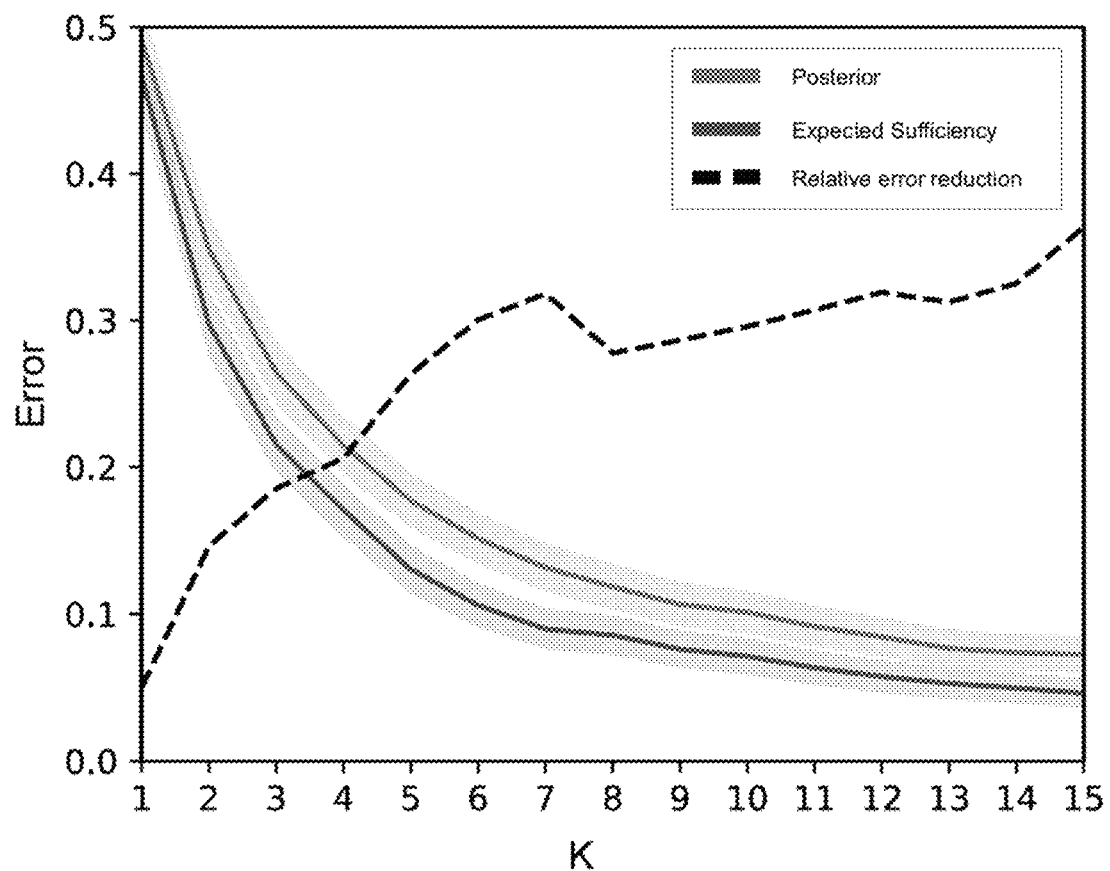
FIG. 11 is a plot showing a comparison of results for counterfactual ranking using expected sufficiency against posterior ranking.

FIG. 11 shows the top k error (1—accuracy) of the counterfactual (darker line) and associative (lighter line) algorithms over all 1671 vignettes vs. k. Shaded regions give 95% confidence intervals. The black dashed line shows the relative reduction in error when switching from the associative to coun¬terfactual algorithm, given by $1 - e_c/e_a$ where $e_a$ is the error rate of the associative algorithm, and $e_c$ is the error rate of the counterfactual algorithm. The results shown in FIG. 11 are for k=1, . . . 15. Complete results may be found in Annex 3.

For k=1, returning the top ranked disease, the counterfactual algorithm achieves a 2.5% higher accuracy than the associative algorithm. For k>1 the performance of the two algorithms diverges, with the counterfactual algorithm giving a large reduction in the error rate over the associative algorithm. For k>5, the counterfactual algorithm reduces the number of misdiagnoses by approximately 30% compared to the associative algorithm. This suggests that the best candidate disease is reasonably well identified by the posterior, but the counterfactual ranking is significantly better at identifying the next most likely diseases. These secondary candidate diseases are especially important in differential diagnosis for the purposes of triage and determining optimal testing and treatment strategies.

A simple method for comparing two rankings is to compare the position of the true disease in the rankings. Across all 1671 vignettes, the counterfactual algorithm ranked the true disease higher than the associative algorithm in 24.7% of vignettes, and lower in only 1.9% of vignettes. On average the true disease is ranked in position 3.16±4.4 by the counterfactual algorithm, a substantial improvement over 3.81±5.25 for the associative algorithm. This is shown in FIG. 12.

FIG. 12 is a table showing the mean position of the true disease for the associative (A) and counterfactual (C) algorithms. The results for expected disablement are almost identical to the expected sufficiency and are included in Annex 3. Results are stratified over the rareness of the disease (given the age and gender of the patient), where VCommon=Very common and VRare=very rare, and All is over all 1671 vignettes regardless of disease rarity. N is the number of vignettes belonging to each rareness category. Mean(X) is the average position of the true disease for algorithm X. Wins (X) is the number of vignettes where algorithm X ranked the true disease higher than its counterpart, and Draws is the number of vignettes where the two algorithms ranked the true disease in the same position. Full results including uncertainties can be found in Annex 3.

In FIG. 12, the vignettes are stratified by the prior incidence rates of the true disease by very common, common, uncommon, rare and very rare. While the counterfactual algorithm achieves significant improvements over the associative algorithm for both common and rare diseases, the improvement is particularly large for rare and very rare diseases, achieving a higher ranking for 29.2% and 32.9% of these vignettes respectively. This improvement is important as rare diseases are typically harder to diagnose and include many serious conditions where diagnostic errors have the greatest consequences.

A second experiment compares the counterfactual and associative algorithms to a cohort of 44 doctors. Each doctor is assigned a set of at least 50 vignettes (average 159), and returns an independent diagnosis for each vignette in the form of a partially ranked list of k diseases, where the size of the list k is chosen by the doctor on a case-by-case basis (average diagnosis size is 2.58 diseases). For a given doctor, and for each vignette diagnosed by the doctor, the associative and counterfactuals algorithms are supplied with the same evidence (excluding the free text case description) and each returns a top-k diagnosis, where k is the size of the diagnosis provided by the doctor. Matching the precision of the doctor for every vignette allows us to compare the accuracy of the doctor and the algorithms without constraining the doctors to give a fixed number of diseases for each diagnosis. This is important, as doctors will naturally vary the size k of their diagnosis to reflect their uncertainty in the diagnostic vignette. The complete results for each of the 44 doctors, and for the posterior, expected disablement, and expected sufficiency ranking algorithms are included in Annex 3.

Figure 13:
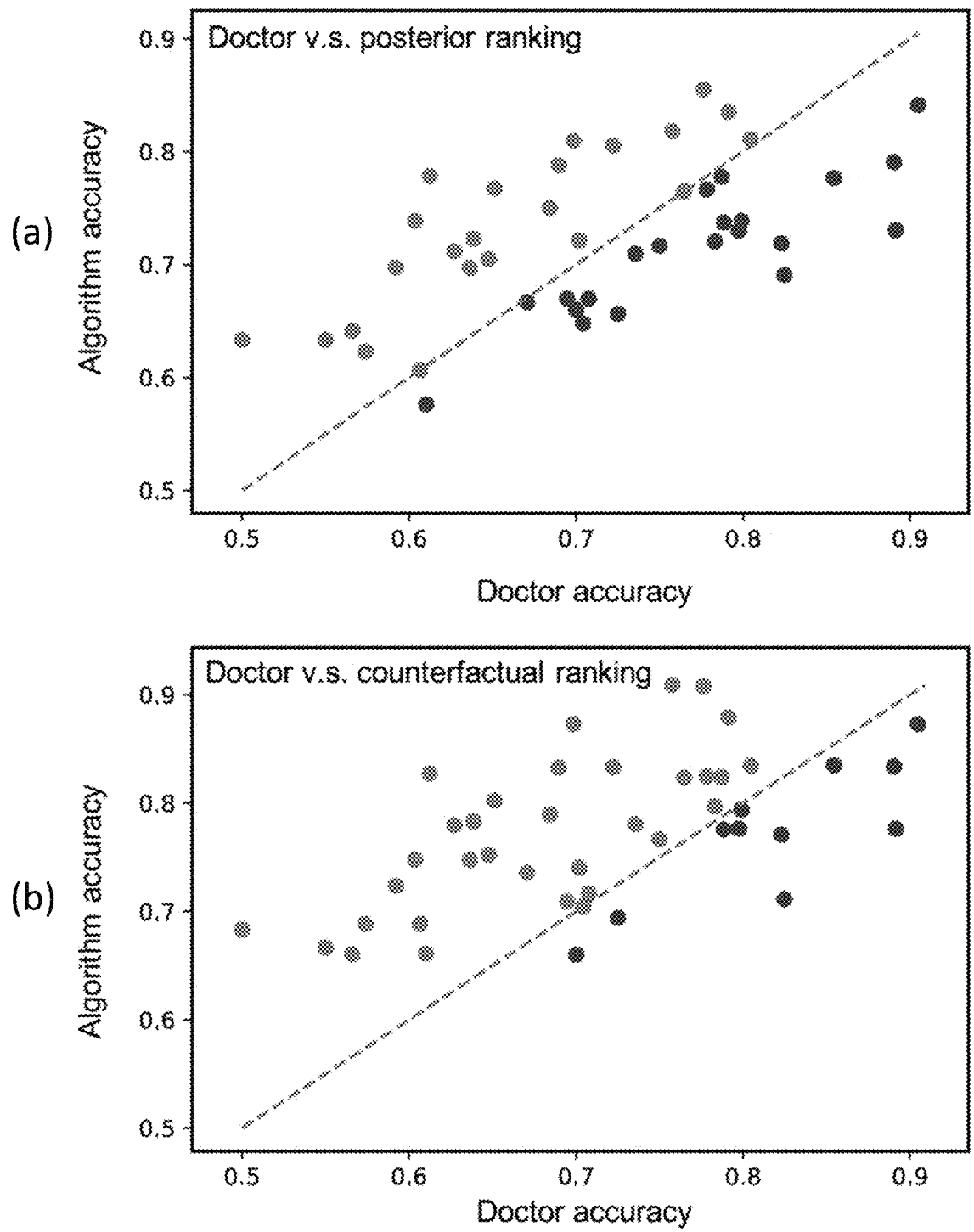
FIG. 13[A] is a plot showing a comparison of results for posterior ranking against doctor ranking.

FIG. 13 compares the accuracy of each doctor to the associative and counterfactual algorithms. Each point gives the average accuracy for one of the 44 doctors, calculated as the proportion of vignettes diagnosed by the doctor where the true disease is included in the doctor's differential. This is plotted against the accuracy that the correspond¬ling algorithm achieved when diagnosing the same vignettes and returning differentials of the same size as that doctor.

Specifically, FIG. 13 shows mean accuracy for each of the 44 doctors, compared to the posterior ranking (top) and expected sufficiency ranking (bottom) algorithms. The line y=x gives a reference for comparing the accuracy of each doctor to the algorithm shadowing them. Points above the line correspond to doctors who achieved a lower accuracy than the algorithm (light gray), points on the line are doctors that achieved the same accuracy as the algorithm (also light gray), and below the line are doctors that achieved higher accuracy than the algorithm (dark gray). The linear correlation can be explained by the variation in the difficulty of the sets of vignettes diagnosed by each doctor. Sets of easier/harder vignettes results in higher/lower doctor and algorithm accuracy scores. As the results for the expected disablement and expected sufficiency are almost identical, only the results for the expected sufficiency are shown. Complete results are listed in Annex 3.

FIG. 14 shows group mean accuracy of doctors and algorithms. The mean accuracy of the doctors D, associative A and counterfactual algorithms (C1=expected sufficiency, C2=expected disablement), averaged over all experiments. $N_{\geq K}$ gives the number of trials (one for each doctor) where this agent achieved a mean accuracy the same or higher than the mean accuracy of agent K∈{D, A, C1, C2}. The bracketed term is the number of trials where the agent scored the same or higher accuracy than agent K to 95% confidence, determined by a one sided binomial test Overall, the associative algorithm performs on par with the average doctor, achieving a mean accuracy across all trails of 72.52±2.97% v.s 71.40±3.01% for doctors. The algorithm scores higher than 21 of the doctors, draws with 2 of the doctors, and scores lower than 21 of the doctors. The counterfactual algorithm achieves a mean accuracy of 77.26±2.79%, considerably higher than the average doctor and the associative algorithm, placing it in the top 25% of doctors in the cohort. The counterfactual algorithm scores higher than 32 of the doctors, draws with 1, and scores a lower accuracy than 12.

The counterfactual algorithm achieves a substantially higher diagnostic accuracy than the associative algorithm. The improvement is particularly pronounced for rare diseases. Whilst the associative algorithm performs on par with the average doctor, the counterfactual algorithm places in the upper quartile of doctors.

Implementations of the subject matter and the operations described in this specification can be realized in digital electronic circuitry, or in computer software, firmware, or hardware, including the structures disclosed in this specification and their structural equivalents, or in combinations of one or more of them. Implementations of the subject matter described in this specification can be realized using one or more computer programs, i.e., one or more modules of computer program instructions, encoded on computer storage medium for execution by, or to control the operation of, data processing apparatus. Alternatively or in addition, the program instructions can be encoded on an artificially-generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, or other storage devices).

In the above embodiments, a purely directed causal discovery algorithm is converted into one that can also detect latent common causes. The modified algorithm is tested extensively on synthetic and real datasets. In the experiments explained above, the modified algorithm maintained the performance of the original algorithm on the directed datasets and allowed algorithms that originally could not detect latent causes to uncover them in both synthetic and real data.

While certain embodiments have been described, these embodiments have been presented by way of example only, and are not intended to limit the scope of the inventions. Indeed the novel methods and systems described herein may be embodied in a variety of other forms; furthermore, various omissions, substitutions and changes in the form of methods and systems described herein may be made without departing from the spirit of the inventions. The accompanying claims and their equivalents are intended to cover such forms of modifications as would fall within the scope and spirit of the inventions.

CLAUSES

Clause 1. A method for providing a computer implemented medical diagnosis, the method comprising:
  receiving an input from a user comprising at least one symptom of the user;
  providing the at least one symptom as an input to a medical model, the medical model being retrieved from memory, the medical model comprising: a probabilistic graphical model comprising probability distributions and relationships between symptoms and diseases;
  performing inference on the probabilistic graphical model to obtain a prediction of the probability that the user has that disease; and
  outputting an indication that the user has a disease from the Bayesian inference, wherein the inference is performed using a counterfactual measure.

Clause 2. A method according to clause 1, wherein the counterfactual measure is the expected disablement Clause 3. A method according to clause 1, wherein the probabilistic graphical model is a NoisyOr model.

Clause 4. A method according to clause 1, wherein the counterfactual measure is the expected disablement and the probabilistic graphical model is a NoisyOr model.

Clause 5. A method according to clause 1, wherein performing inference comprises using a discriminative model pretrained to approximate the probabilistic graphical model, the discriminative model being trained using samples from said probabilistic graphical model; deriving estimates, from the discriminative model, that the user has a disease;

performing approximate inference on the probabilistic graphical model to obtain an indication that the user has that disease using the estimate from the discriminative model.

Clause 6. A method according to clause 1, wherein the results of predictions of the diseases from the probabilistic graphical model are ranked using the counterfactual measure.

Clause 7. A method according to clause 1, wherein the probabilistic graphical model is a twin network.

Clause 8. A method according to clause 1, wherein probabilistic graphical model is a twin network, and the counterfactual measure is the expected disablement.

Clause 9. A method according to clause 1, wherein probabilistic graphical model is a twin network, the counterfactual measure is the expected disablement and the probabilistic graphical model is a NoisyOr model.

Clause 10. A system for providing a computer implemented medical diagnosis, the system comprising a processor and a memory, the processor being adapted to:

receive an input from a user comprising at least one symptom of the user;

provide the at least one symptom as an input to a medical model, the medical model being retrieved from memory, the medical model comprising:

a probabilistic graphical model being stored in memory comprising probability distributions and relationships between symptoms and diseases, perform inference on the probabilistic graphical model to obtain a prediction of the probability that the user has that disease; and output an indication that the user has a disease from the Bayesian inference, wherein the inference is performed using a counterfactual measure.

Clause 11. A non-transitory carrier medium carrying computer readable instructions being adapted to cause a computer to run the method recited in clause 1.

Clause 12. A method of forming a twin model that is a graphical representation for computing a counterfactual measure for medical diagnosis, the method comprising:

receiving a set of data;

creating a first graphical representation from the set of data, the first graphical representation comprising a plurality of first nodes indicating symptoms, risk factors and diseases, the first graphical representation indicating a relationship between the symptoms, the risk factors and the diseases;

creating a second graphical representation, wherein the second graphical representation is a copy of the first graphical representation, the second graphical representation comprising a plurality of second nodes indicating the symptoms, the risk factors and the diseases;

combining the first graphical representation and the second graphical representation to create said twin model; and setting an intervention node of the plurality of second nodes in the twin model to a value so that inference can be performed on the twin model to obtain a prediction of the probability that a user of the model has a specified disease.

Clause 13. A method according to clause 12 wherein each node in the plurality of first nodes is associated with a latent variable, the method further comprising:

linking the first graphical representation and the second graphical representation by sharing the latent variables of each node of the plurality of first nodes with a corresponding node in the plurality of second nodes.

Clause 14. A method according to clause 12 or 13, wherein the first graphical representation and the second graphical representation are probabilistic graphical models.

Clause 15. A method according to clause 12 or 13, wherein the first graphical representation and the second graphical representation are NoisyOr models.

Clause 16. A method according to clause 12 further comprising:

merging a node from the plurality of first nodes with its corresponding node in the plurality of second nodes so as to simplify the twin model.

Clause 17. A method according to clause 13 further comprising:

merging a node from the plurality of first nodes with its corresponding node in the plurality of second nodes so as to simplify the twin model.

Clause 18. A method according to clause 17, after setting the intervention node of the plurality of second nodes in the twin model to a value, the method further comprising:

when a node from the plurality of second nodes has identical latent variables and identical parent nodes as its corresponding node in the plurality of first nodes, merging the node with its corresponding node so as to simplify the twin model.

The invention claimed is:

1. A method for providing a computer implemented medical diagnosis, the method comprising:

receiving an input from a user comprising at least one symptom of the user;

providing the at least one symptom as an input to a medical model, the medical model being retrieved from memory, the medical model comprising: a probabilistic graphical model comprising probability distributions and causal relationships between symptoms and diseases;

performing counterfactual inference on the probabilistic graphical model to obtain a prediction of the probability that the user has a disease; and outputting a counterfactual measure determined from the counterfactual inference, wherein the counterfactual measure is based on whether one or more symptoms would be expected to be present if a first one or more diseases were cured;

wherein the probabilistic graphical model is a twin network, the twin network formed by:

creating a first graphical representation from a set of data, the first graphical representation comprising a plurality of first nodes indicating symptoms, risk factors and diseases, the first graphical representation indicating a relationship between the symptoms, the risk factors and the diseases, the first graphical representation indicating real variables;

creating a second graphical representation, wherein the second graphical representation is a copy of the first graphical representation, the second graphical representation comprising a plurality of second nodes indicating the symptoms, the risk factors and the diseases, the second graphical representation indicating counterfactual states of the real variables; and combining the first graphical representation and the second graphical representation by the sharing of exogenous causes to create said twin network.

2. The method of claim 1, wherein the counterfactual measure is for a second one or more diseases, and wherein the first one or more diseases are possible causes of the one or more symptoms other than the second one or more diseases.

3. The method of claim 1, wherein the counterfactual measure is for the first one or more diseases.

4. The method of claim 1, wherein the counterfactual measure is based on the number of the one or more symptoms that would be expected to be present if the one or more diseases were cured.

5. The method of claim 1, wherein the counterfactual measure is based on the number of the one or more symptoms that would not be expected to be present if the one or more diseases were cured.

6. The method of claim 1, wherein the counterfactual measure is based on the probability that the one or more symptoms would be present if the one or more diseases were cured.

7. The method of claim 1, wherein the counterfactual measure is based on the probability that the one or more symptoms would not be present if the one or more diseases were cured.

8. The method of claim 1, wherein the counterfactual measure is an expected sufficiency.

9. The method of claim 1, wherein the counterfactual measure is an expected disablement.

10. The method of claim 1, wherein the probabilistic graphical model is a NoisyOr model.

11. The method of claim 1, wherein performing counterfactual inference comprises using a discriminative model pre-trained to approximate the probabilistic graphical model, the discriminative model being trained using samples from said probabilistic graphical model; deriving estimates, from the discriminative model, that the user has a disease; performing approximate inference on the probabilistic graphical model to obtain an indication that the user has that disease using the estimate from the discriminative model.

12. The method of claim 1, wherein results of predictions of diseases from the probabilistic graphical model are ranked using the counterfactual measure.

13. The method of claim 1, wherein the probabilistic graphical model is a twin network, and the probabilistic graphical model is a NoisyOr model.

14. The method of claim 1, wherein the counterfactual inference further comprises:
  (1) an abduction step comprising updating a distribution of exogenous latent variables in the twin network based on the at least one symptom;
  (2) an action step comprising applying a do-operation to a node indicating the disease in the second representation of the updated twin model updated from (1); and
  (3) a prediction step comprising using the modified twin network from (2) to compute the probability that the user would have the disease.

15. A system for providing a computer implemented medical diagnosis, the system comprising a processor and a memory, the processor being adapted to:
  receive an input from a user comprising at least one symptom of the user;
  provide the at least one symptom as an input to a medical model, the medical model being retrieved from memory, the medical model comprising:
    a probabilistic graphical model being stored in memory comprising probability distributions and causal relationships between symptoms and diseases,
  perform counterfactual inference on the probabilistic graphical model to obtain a prediction of the probability that the user has a disease; and
  output a counterfactual measure determined from the counterfactual inference, wherein, the counterfactual measure is based on whether one or more symptoms would be expected to be present if a first one or more diseases were cured,
  wherein the probabilistic graphical model is a twin network, the twin network formed by:
    creating a first graphical representation from a set of data, the first graphical representation comprising a plurality of first nodes indicating symptoms, risk factors and diseases, the first graphical representation indicating a relationship between the symptoms, the risk factors and the diseases, the first graphical representation indicating real variables;
    creating a second graphical representation, wherein the second graphical representation is a copy of the first graphical representation, the second graphical representation comprising a plurality of second nodes indicating the symptoms, the risk factors and the diseases, the second graphical representation indicating counterfactual states of the real variables; and
    combining the first graphical representation and the second graphical representation by the sharing of exogenous causes to create said twin network.

16. A non-transitory carrier medium carrying computer readable instructions being adapted to cause a computer to perform:
  receiving an input from a user comprising at least one symptom of the user;
  providing the at least one symptom as an input to a medical model, the medical model being retrieved from memory, the medical model comprising: a probabilistic graphical model comprising probability distributions and causal relationships between symptoms and diseases;
  performing counterfactual inference on the probabilistic graphical model to obtain a prediction of the probability that the user has a disease; and
  outputting a counterfactual measure determined from the counterfactual inference, wherein, the counterfactual measure is based on whether one or more symptoms would be expected to be present if a first one or more diseases were cured,
  wherein the probabilistic graphical model is a twin network, the twin network formed by:
    creating a first graphical representation from a set of data, the first graphical representation comprising a plurality of first nodes indicating symptoms, risk factors and diseases, the first graphical representation indicating a relationship between the symptoms, the risk factors and the diseases, the first graphical representation indicating real variables;
    creating a second graphical representation, wherein the second graphical representation is a copy of the first graphical representation, the second graphical representation comprising a plurality of second nodes indicating the symptoms, the risk factors and the diseases, the second graphical representation indicating counterfactual states of the real variables; and
    combining the first graphical representation and the second graphical representation by the sharing of exogenous causes to create said twin network.

17. The non-transitory carrier medium of claim 16, wherein the counterfactual measure is for a second one or more diseases, and wherein the first one or more diseases are possible causes of the one or more symptoms other than the second one or more diseases.

18. The non-transitory carrier medium of claim 16, wherein the counterfactual measure is the number of the one or more symptoms that would be expected to be present if the one or more diseases were cured.

19. The non-transitory carrier medium of claim 16, wherein the counterfactual measure is the expected sufficiency.

20. The non-transitory carrier medium of claim 16, wherein the probabilistic graphical model is a Noisy-Or model.

* * * * *